(12) United States Patent
Adermann et al.

(10) Patent No.: US 7,655,629 B2
(45) Date of Patent: Feb. 2, 2010

(54) PEPTIDES AND THEIR USE FOR THE TREATMENT OF HIV INFECTIONS

(75) Inventors: Knut Adermann, Hannover (DE); Frank Kirchhoff, Ulm (DE); Jan Münch, Ulm (DE); Axel Schulz, Hannover (DE)

(73) Assignee: IPF Pharmaceuticals GmbH, Hannover (DE)

( * ) Notice: Subject to any disclaimer, the term of this patent is extended or adjusted under 35 U.S.C. 154(b) by 500 days.

(21) Appl. No.: 10/539,627

(22) PCT Filed: Dec. 19, 2003

(86) PCT No.: PCT/EP03/14654

§ 371 (c)(1),
(2), (4) Date: Sep. 19, 2005

(87) PCT Pub. No.: WO2004/056871

PCT Pub. Date: Jul. 8, 2004

(65) Prior Publication Data

US 2007/0072805 A1   Mar. 29, 2007

(30) Foreign Application Priority Data

Dec. 19, 2002   (EP) .................................. 02028465

(51) Int. Cl.
*A61K 38/00* (2006.01)
*A61K 38/04* (2006.01)
*A61K 51/00* (2006.01)
*A61M 36/14* (2006.01)
*C12Q 1/70* (2006.01)

(52) U.S. Cl. .......................... 514/13; 530/324; 530/326; 424/1.69; 435/5

(58) Field of Classification Search ..................... 514/13
See application file for complete search history.

(56) References Cited

U.S. PATENT DOCUMENTS 6,200,801 B1 * 3/2001 Ferkol et al. ............. 435/320.1

FOREIGN PATENT DOCUMENTS

| WO | WO 92/18141 | 10/1992 |
|---|---|---|
| WO | WO 01/08708 | 2/2001 |
| WO | WO 01/34640 | 5/2001 |

OTHER PUBLICATIONS

Shapiro, et al., "Alpha-1-antitrypsin inhibits human immunodeficiency virus type 1," FASEB Journal, Fed. Of American Soc. For Experimental Biology, vol. 15, No. 1, Jan. 2001, p. 115-122, [XP002164955].
Detheux, et al., Journal of Experimental Medicine, s. example 3), 2000.
J. Gante, Peptidomimetics-tailored enzyme inhibitors, Angewandte Chemie International Edition 33, 1994, 1699-1720.
F. Tratar, Arkivoc 2001, 7-20, free access via internet under http://www.arkat-usa.org/ark/journal/2001/I05_Tisler/187/0109_index.asp, 2001.
H.D. Jakubke, Peptide, Spektrum Akademischer Verlag, 1996, 00. 286-296.
G.B. Wisdom (editor), Peptide Antigens—A Practical Approach, 1994, Oxford University Press, New York, pp. 117-179.

* cited by examiner

*Primary Examiner*—Cecilia Tsang
*Assistant Examiner*—Maury Audet
(74) *Attorney, Agent, or Firm*—Jacobson Holman PLLC

(57) ABSTRACT

The invention relates to peptides with biological activity against infection having the amino acid sequence $Z_1$-LE-$X_1$-IP-$X_2$-$X_3$-$X_4$-P-$X_5$-$X_6$-$X_7$-$X_8$-$X_9$-$X_{10}$-K-$X_{11}$-$X_{12}$-$X_{13}$-$X_{14}$-$X_{15}$-$Z_2$, wherein $X_1$ is a lysine, alanine, or aspartic acid; $X_2$ is a cysteine, methionine or isoleucine; $X_3$ is a serine, cysteine, lysine or glycine; $X_4$ is an isoleucine, alanine, phenylalanine or cysteine; $X_5$ is a proline, D-proline or a substituted L- or D-proline; $X_6$ is a cysteine or glutamic acid; $X_7$ is an amino acid with a hydrophobic or an aromatic side chain or cysteine; $X_8$ is an amino acid with a hydrophobic or an aromatic side chain or cysteine; $X_9$ is an amino acid with an aromatic side chain; $X_{10}$ is a glycine, alanine or asparagine; $X_{11}$ is a proline, aspartic acid, octahydroindolyl-2-carboxylic acid or D-1,2,3,4-tetrahydroisoquinoline-3-carboxylic acid; $X_{12}$ is a phenylalanine, alanine, glycine, glutamic acid or D-1,2,3,4-tetrahydroisoquinoline-3-carboxylic acid; $X_{13}$ is an amino acid with a hydrophobic or an aromatic side chain; $X_{14}$ is an amino acid with a hydrophobic or an aromatic side chain; $X_{15}$ is a phenylalanine or deletion; $Z_1$ is $NH_2$ or a sequence of 1 to 10 amino acid residues; $Z_2$ is COOH or a sequence of 1 to 10 amino acid residues; and peptides which are fragments and/or covalently linked oligomers and/or derivatives, especially amidated, alkylated, acylated, sulfated, pegylated, phosphorylated and/or glycosylated derivatives, and mutants thereof, and with the provisio that (a) if $X_{12}$ is alanine, glycine, glutamic acid, or D-1,2,3,4-tetrahydroisoquinoline-3-carboxylic acid than $X_{13}$, $X_{14}$ and $X_{15}$ are phenylalanine, valine and phenylalanine respectively; and/or (b) if $X_{12}$ is phenylalanine, than $X_{13}$, $X_{14}$ and $X_{15}$ are valine, phenylalanine and a deletion, respectively; and (c) that there are at maximum two cysteine residues in a peptide.

7 Claims, 4 Drawing Sheets

PEPTIDES AND THEIR USE FOR THE TREATMENT OF HIV INFECTIONS

This is a 371 of PCT/EP03/14654, filed 19 Dec. 2003.

The present invention relates to peptides which exhibit inhibitory activity on the infection of human cells by human immunodeficiency virus (HIV).

TECHNICAL BACKGROUND

In the last years, intensive research for therapeutics with activity against infection by HIV was performed. Several medicaments were developed and tested, which delay and suppress the outbreak of AIDS and lower the level of the HIV in blood. In the US the life-span of HIV-infected patients after the outbreak of AIDS was raised from 11 month in 1984 to 46 month in 1997. In the search for therapeutics various strategies were applied, which lead to several classes of medicaments such as the protease-blockers inhibiting a protease, which the virus requires for replication, and medicaments inhibiting the viral reverse transcriptase, which is essential for the replication of retroviruses. A group of active agents developed only recently are fusion inhibitors, which shall prevent the entry of the virus into cells. It was also shown that the provision of interleukin-2 in combination with other active agents could increase the strength of the immune response.

Entry inhibitors block the uptake of HIV viral particles into blood cells by blocking one of the molecular steps occurring during viral entry. An important step is binding of HIV to one of the major chemokine coreceptors CCR5 and CXCR4 (CC chemokine receptor 5 and CXCR chemokine receptor 4). These coreceptors are located on the surface of blood cells and are required to bind to HIV envelope proteins before viral entry. Another step of viral interaction with cells required for fusion is the binding of the HIV envelope protein gp120 to cellular CD4 receptors. These steps are often referred to as attachment of the viral particle to cellular targets. The blocking of the binding of HIV to chemokine coreceptors has been shown to suppress viral entry (Strizki J. M., Proc. Natl. Acad. Sci. USA, 2001, 98, 12718-12723). The same was reported by blocking the interaction of gp120 with CD4 receptors (Lin et al., Proc. Natl. Acad. Sci. USA, 2003, 100, 11013-11018). The HIV protein gp41 has also been recognised as a potential target for anti-HIV drug development (Gordon et al., AIDS Research and Human Retroviruses 11, 677-686, 1995). The first approved fusion inhibitor is enfuvirtide (T-20, Fuzeon, DP178) (WO 01/51673 A2; WO 96/40191; Cervia J. S. et al., Clin. Infect. Dis, 2003, 37, 1102-1106; Kilby J. M., Nature Medicine, 1998, 4, 1302-1307). This fusion inhibitor is identical to a part of the HIV envelope protein gp41 called HR-2 and inhibits HIV-cell fusion by binding to the HR-1 segment (HR=heptad repeat) of gp41 (FIG. 4), thus preventing the binding of HR-2 to the HR-1 segment of gp41 which in turn prevents the formation of a six-helix bundle required for fusion of the viral particle and the blood cell. T-20 has not been shown to bind to protein segments other than HR-1 of HIV gp41 or even other molecules of viral or eukaryotic origin. A further agent with biological activity against HIV was recently described in WO 01/34640. Disclosed is a peptide of 20 amino acids named VIRIP (virus inhibiting peptide), which was isolated from human hemofiltrate and found to inhibit the infection of human cells by HIV.

Despite those efforts and different available medication, the problem remains unsolved that there is still no cure against AIDS, because the known therapeutics, though capable of significantly lowering the level of HIV in the body and of HIV-infected blood cells, do not remove the virus entirely. A special drawback is, that the HIV is especially prone to mutations, which often result in the development of resistance against certain therapeutics. In general, the known therapeutics are only sufficiently effective if they are administered in combination with other therapeutics. Such combined therapies at present extend the lifespan of the average patient without providing a cure, and are generally accompanied by severe side effects and frequently do not allow the patient to lead a "normal" life.

There is a great medical need to provide new therapeutics and improved therapeutics, which will lead to improved therapies, less side effects, and significant extension of the life expectancy of those infected by HIV, before or after the outbreak of AIDS.

The present invention faces the problem to provide new therapeutics, which will overcome the problems as described above, and will allow an efficient therapy or will contribute to an efficient combination therapy.

SUMMARY OF THE INVENTION

Surprisingly, the problem is solved by peptides provided by the present invention, which interact at least with the fusion peptide of HIV gp41. The fusion peptide is the very amino-terminal part of gp41 consisting of about 30 amino acid residues. In a current model, the hydrophobic fusion peptide of gp41 serves as an anchor connecting the viral particle with the cellular host membrane (Dimitrov A. S. et al., Biochemistry, 2003, 42, 14150-14158; Mobley et al., Biochim. Biophys. Acta, 1999, 1418, 1-18), and the peptides of the present invention interfere with the HIV cell fusion process, and thus prevent viral entry.

The peptides of the present invention are those with a biological activity against HIV infection, having amino acid sequence

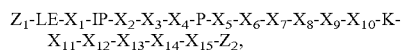

wherein $X_1$ is a lysine, alanine, or aspartic acid;
$X_2$ is a cysteine, methionine or isoleucine;
$X_3$ is a serine, cysteine, lysine or glycine;
$X_4$ is an isoleucine, alanine, phenylalanine or cysteine;
$X_5$ is a proline, D-proline or a substituted L- or D-proline;
$X_6$ is a cysteine or glutamic acid;
$X_7$ is an amino acid with a hydrophobic or an aromatic side chain or cysteine;
$X_8$ is an amino acid with a hydrophobic or an aromatic side chain or cysteine;
$X_9$ is an amino acid with an aromatic side chain;
$X_{10}$ is a glycine, alanine or asparagine;
$X_{11}$ is a proline, aspartic acid, octahydroindolyl-2-carboxylic acid or D-1,2,3,4-tetrahydroisoquinoline-3-carboxylic acid;
$X_{12}$ is a phenylalanine, alanine, glycine, glutamic acid or D-1,2,3,4-tetrahydroisoquinoline-3-carboxylic acid;
$X_{13}$ is an amino acid with a hydrophobic or an aromatic side chain;
$X_{14}$ is an amino acid with a hydrophobic or an aromatic side chain;
$X_{15}$ is a phenylalanine or deletion;
$Z_1$ is $NH_2$ or a sequence of 1 to 10 amino acid residues;
$Z_2$ is COOH or a sequence of 1 to 10 amino acid residues;

and peptides which are fragments and/or covalently linked oligomers and/or derivatives, especially amidated, alkylated, acylated, sulfated, pegylated, phosphorylated and/or glycosylated derivatives, and mutants thereof, with the provisio that (a) if $X_{12}$ is alanine, glycine, glutamic acid, or D-1,2,3,4-tetrahydroisoquinoline-3-carboxylic acid then $X_{13}$, $X_{14}$ and $X_{15}$ are phenylalanine, valine and phenylalanine respectively; and/or (b) if $X_{12}$ is phenylalanine, then $X_{13}$, $X_{14}$ and $X_{15}$ are valine, phenylalanine and a deletion, respectively; and (c) that there are at maximum two cysteine residues in a peptide.

In a preferred embodiment of the above peptide with the generic formula $$Z_1\text{-LE-}X_1\text{-IP-}X_2\text{-}X_3\text{-}X_4\text{-P-}X_5\text{-}X_6\text{-}X_7\text{-}X_8\text{-}X_9\text{-}X_{10}\text{-K-}X_{11}\text{-}X_{12}\text{-}X_{13}\text{-}X_{14}\text{-}X_{15}\text{-}Z_2,$$

$X_7$ is phenylalanine, cysteine, valine, isoleucine, leucine, 3,3-diphenylalanine, 1-naphthylalanine, or p-fluorophenylalanine; $X_8$ is a phenylalanine, leucine, alanine, tryptophan, glycine, cysteine, D-1,2,3,4-tetrahydroisoquinoline-3-carboxylic acid or L-1,2,3,4-tetrahydroisoquinoline-3-carboxylic acid; $X_9$ is a phenylalanine or D-1,2,3,4-tetrahydroisoquinoline-3-carboxylic acid; and $Z_1$ is preferably $NH_2$ or a sequence of 1 to 3 amino acid residues and $Z_2$ is preferably COOH or a sequence of 1 to 3 amino acid residues. The biological activity against HIV infection of the above peptides, as measured as $IC_{50}$, is equal of or below of 6500 nM.

A further embodiment are peptides according to the invention with a biological activity against infection by HIV, having the amino acid sequence $$Z_1\text{-LE-}X_1\text{-IP-}X_1\text{-}X_3\text{-}X_4\text{-P-}X_5\text{-}X_6\text{-}X_7\text{-}X_8\text{-}X_9\text{-}X_{10}\text{-K-}X_{11}\text{-FVF-}Z_2,$$

wherein
$X_1$ is a lysine, alanine or aspartic acid;
$X_2$ is a cysteine, methionine or isoleucine;
$X_3$ is a serine, cysteine or glycine;
$X_4$ is an isoleucine or cysteine;
$X_5$ is a proline, D-proline or any substituted L- or D-proline;
$X_6$ is a cysteine or glutamic acid;
$X_7$ is a phenylalanine, cysteine, valine, isoleucine or 3,3-diphenyl-alanine;
$X_8$ is a phenylalanine, leucine, alanine, glycine, cysteine, D-1,2,3,4-tetrahydroisoquinoline-3-carboxylic acid or L-1,2,3,4-tetrahydro-isoquinoline-3-carboxylic acid;
$X_9$ is an amino acid with an aromatic side chain;
$X_{10}$ is a glycine or asparagine;
$X_{11}$ is a proline or D-1,2,3,4-tetrahydroisoquinoline-3-carboxylic;
$Z_1$ is $NH_2$ or a sequence of 1 to 10 amino acid residues;
$Z_2$ is COOH or a sequence of 1 to 10 amino acid residues;

and peptides which are fragments and/or covalently linked oligomers and/or derivatives, especially amidated, alkylated, acylated, sulfated, pegylated, phosphorylated and/or glycosylated derivatives, and mutants thereof, with the provisio that (a) if two cysteine residues are present, said residues are separated by four other amino acid residues; and (b) if L-1,2,3,4-tetrahydroisoquinoline-3-carboxylic acid, D-1,2,3,4-tetrahydroisoquinoline-3-carboxylic acid and/or 3,3-diphenyl-alanine are present, no cysteine residue is present.

In a preferred embodiment of the above peptide with the generic formula $Z_1\text{-LE-}X_1\text{-IP-}X_3\text{-}X_4\text{-P-}X_5\text{-}X_6\text{-}X_7\text{-}X_8\text{-}X_9\text{-}X_{10}\text{-K-}X_{11}\text{-FVF-}Z_2$, $X_9$ is a phenylalanine or D-1,2,3,4-tetrahydroisoquinoline-3-carboxylic acid, $Z_1$ is preferably $NH_2$ or a sequence of 1 to 3 amino acid residues and $Z_2$ is preferably COOH or a sequence of 1 to 3 amino acid residues. The biological activity against HIV infection of the above peptide, as measured as $IC_{50}$, is equal of or below of 2000 nM.

An even further embodiment are peptides according the invention with a biological activity against infection by HIV, having the amino acid sequence $$Z_1\text{-LE-}X_2\text{-IP-}X_2\text{-}X_3\text{-IP-}X_5\text{-}X_6\text{-}X_7\text{-}X_8\text{-F-}X_{10}\text{-KPFVF-}Z_2,$$

wherein
$X_1$ is a lysine, alanine or aspartic acid;
$X_2$ is a cysteine, methionine or isoleucine;
$X_3$ is a serine or glycine;
$X_5$ is a L-proline, D-proline or any substituted L- or D-proline
$X_6$ is a cysteine or glutamic acid;
$X_7$ is a phenylalanine or valine;
$X_8$ is a phenylalanine, leucine, alanine or L-1,2,3,4-tetrahydro-isoquinoline-3-carboxylic acid;
$X_{10}$ is a glycine or asparagine;
$Z_1$ is $NH_2$ or a sequence of 1 to 10 amino acid residues;
$Z_2$ is COOH or a sequence of 1 to 10 amino acid residues;

and peptides which are fragments and/or covalently linked oligomers and/or derivatives, especially amidated, alkylated, acylated, sulfated, pegylated, phosphorylated and/or glycosylated derivatives, and mutants thereof.

In a preferred embodiment of the peptide with the generic formula $Z_1\text{-LE-}X_2\text{-IP-}X_2\text{-}X_3\text{-IP-}X_5\text{-}X_6\text{-}X_7\text{-}X_8\text{-F-}X_{10}\text{-KPFVF-}Z_2$, $Z_1$ is preferably $NH_2$ or a sequence of 1 to 3 amino acid residues and $Z_2$ is preferably COOH or a sequence of 1 to 3 amino acid residues. The biological activity against HIV infection of the peptide, as measured as $IC_{50}$, is equal of or below of 800 nM.

An even further embodiment are peptides of the invention with biological activity against infection by HIV, having the amino acid sequence $$Z_1\text{-LEAIP-}X_2\text{-SIP-}X_5\text{-}X_6\text{-V-}X_8\text{-FNKPFVF-}Z_2,$$

wherein
$X_2$ and $X_6$ are cysteines, or $X_2$ is methionine and $X_6$ is glutamic acid
$X_5$ is a D-proline or L-proline;
$X_8$ is an amino acid with a hydrophobic or an aromatic side chain or lysine;
$Z_1$ is $NH_2$ or a sequence of 1 to 10 amino acid residues;
$Z_2$ is COOH or a sequence of 1 to 10 amino acid residues;

and peptides which are fragments and/or covalently linked oligomers and/or derivatives, especially amidated, alkylated, acylated, sulfated, pegylated, phosphorylated and/or glycosylated derivatives, and mutants thereof, with the proviso that at least one of the following is true:
$X_2$ is proline or
$X_5$ is not leucine or
$X_6$ and $X_8$ are cysteine.

In a preferred embodiment of the peptide with the generic formula $Z_1\text{-LEAIP-}X_2\text{-SIP-}X_5\text{-}X_6\text{-V-}X_8\text{-FNKPFVF-}Z_2$, $Z_1$ is preferably $NH_2$ or a sequence of 1 to 3 amino acid residues and $Z_2$ is preferably COOH or a sequence of 1 to 3 amino acid residues.

Also an embodiment of the peptides of the present invention are those, wherein the cysteine residues at positions 6 and 11, 6 and 12, 7 and 12, or 8 and 13 are connected by an intramolecular disulfide bond. The peptides with cysteine residues at these positions may occur with an intramolecular bridge between these residues, or, under reductive conditions as linear molecules. A further embodiment are peptides with a single cysteine residue, wherein said cysteine residue is connected by an inter-molecular disulfide bond to another peptide molecule with a single cysteine residue, forming a homo-dimer. Also embodiments are those peptides, wherein the leucine residue at amino acid position 1 and the glutamic acid at amino acid position 2 are covalently linked by an N-alkylated amide bond or by an ester bond or by a reduced peptide bond or by a retro-inverso peptide bond or by an N-alkylated retro-inverso peptide bond. A further embodiment are peptides which interact with the HIV fusion peptide of gp41. The peptides of the present invention are characterised by an $IC_{50}$ of equal or below 6500 nM, preferably an $IC_{50}$ of equal or below 2000 nM and most preferably an $IC_{50}$ of equal or below 800 nM, such as VIR-344 (SEQ ID NO. 49) with an $IC_{50}$ of 348 nM, VIR-345 (SEQ ID NO. 50) with an $IC_{50}$ of 298 nM, VIR-353 (SEQ ID NO. 56) with an $IC_{50}$ of 225 nM, VIR-357 (SEQ ID NO. 60) with an $IC_{50}$ of 497 nM, VIR-358 (SEQ ID NO. 61) with an $IC_{50}$ of 706 nM, VIR-449 (SEQ ID NO 73) with an $IC_{50}$ of 274 nM, VIR-455 (SEQ ID NO 76) with an $IC_{50}$ of 134 nM, VIR-484 (SEQ ID NO 79) with an $IC_{50}$ of 100 nM, VIR-512 (SEQ ID NO. 83) with an $IC_{50}$ of 138 nM, VIR-576 (SEQ ID NO: 86) with an $IC_{50}$ of 107 nM and VIR-580 (SEQ ID NO. 87) with an $IC_{50}$ of 150 nM.

Also the nucleic acids coding for these peptides are embodiments of the present invention. Further embodiments are antibodies binding specifically to these peptides. A further embodiment is a medicament containing anyone of these peptides, nucleic acids coding for these peptides, or specific antibodies directed against these peptides. In one embodiment the medicament is in galenic formulations for oral, intravenous, intramuscular, intracutaneous, subcutaneous, intrathecal administration, and as an aerosol for transpulmonary administration. A further embodiment is said medicament comprising at least one further therapeutic agent. Also an embodiment is the medicament, wherein the said at least one further therapeutic agent is a viral protease inhibitor, a reverse transcriptase inhibitor, a fusion inhibitor, a cytokine, a cytokine inhibitor, a glycosylation inhibitor or a viral mRNA inhibitor, etc. Use of these peptides for the manufacturing of a medicament for the treatment of HIV infections is a further embodiment. Also an embodiment is an assay for determining molecules capable of interacting with the fusion peptide of HIV, comprising anyone of the above peptides of the invention. Use of these peptides in said assay is also an embodiment. A further embodiment is a diagnostic agent containing these peptides, nucleic acids or antibodies. One more embodiment is use of the diagnostic agent for assay systems for testing isolated plasma, tissue, urine and cerebrospinal fluid levels for HIV infection. Further specific embodiments of the present invention are the peptides according to claim 8.

DETAILED DESCRIPTION OF THE INVENTION

Figure 1:
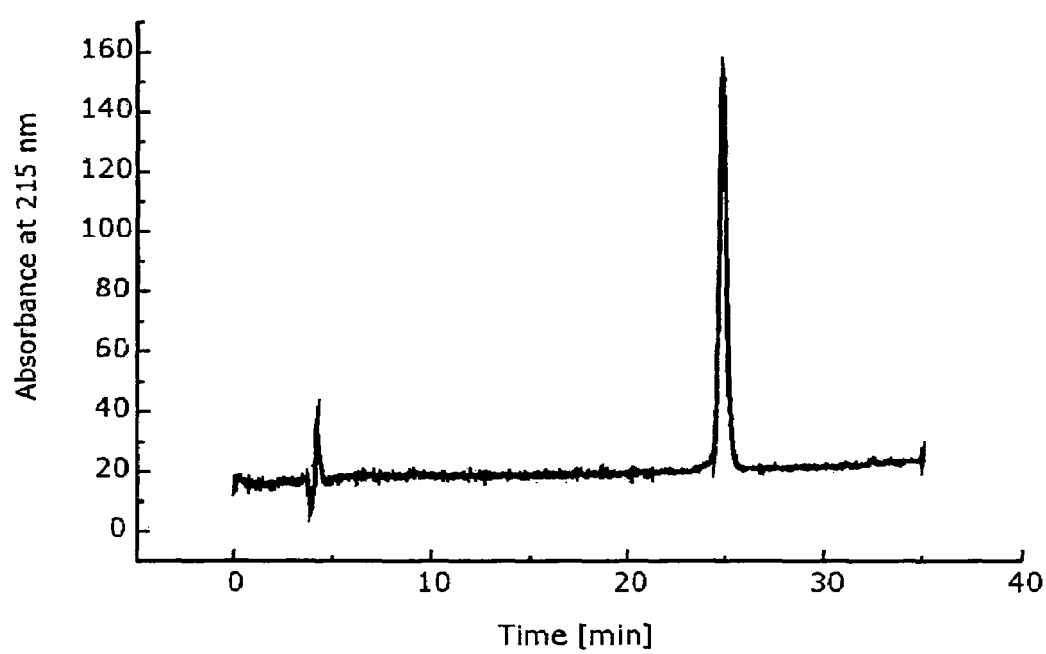
FIG. 1: C18 HPLC trace of purified VIR-199 (sequence: LEAIPMSIPpEFLFNKPFVF) (SEQ ID NO. 18). Conditions: Vydac C18 (4.6×250 mm, 300 Å, 5 μm, flow rate: 0.8 ml/min, gradient: 10-70 volume % B in 30 min, buffer A: 0.07 volume % TFA, buffer B: 0.05 volume % TFA, 80 volume % acetonitrile).

The peptides of the present invention are related to the hemofiltrate-derived peptide VIRIP (SEQ ID No. 1) as disclosed and described in WO 01/34640, which has biological activity in preventing infection by HIV. They all differ from VIRIP at least in amino acid position 13, where VIRIP contains a lysine residue, while the peptides of the present invention do not contain a lysine residue at amino acid position 13. In addition to that, the peptides of the present invention have further amino acid changes throughout their 21 amino acids in comparison to VIRIP. The peptides of the present invention all posses significantly higher anti-HIV activity (measured as $IC_{50}$ against two HIV-1 strains) than VIRIP. The increase in anti-HIV activity is at least 4-fold (VIR-184, SEQ ID NO. 12), and the very active peptides of the present invention are up to 161-fold (e.g. VIR-280, SEQ ID NO. 39) more active against HIV than VIRIP.

The peptides of the invention are based on an amino acid sequence of 21 amino acids, with possible extensions of 1 to 10 amino acids at both ends according to $Z_1$ and $Z_2$, whereby an extension of 3 amino acids is preferred. The amino acid numbering used herein always corresponds to the amino acids 1 to 21 of the basic sequence irrespective of a possible N-terminal extension due to a residue $Z_1$, such that amino acid position 1 corresponds to leucine and amino acid position 21 to phenylalanine or a deletion. The common amino acid one and three letter codes are used. If not indicated otherwise, the L-enantiomers of amino acids were used. The small letter "p" stands for D-proline. Other D-enantiomers are indicated by a "D-" prefix. "Tic" stands for tetrahydrisioquinoline carboxylic acid. "Oic" stands for octahydroindole carboxylic acid.

The term "hydrophobic amino acid" as used herein is readily understood by the skilled person. In particular, it refers to any of the amino acids glycine, alanine, valine, leucine, isoleucine, methionine, proline, phenylalanine, tyrosine, tryptophan, and non-endogenous hydrophobic amino acids.

The term "aromatic amino acid" as used herein is readily understood by the skilled person. In particular it refers to any of the amino acids phenylalanine, tyrosine, tryptophan, histidine, and non-endogenous aromatic amino acids, such as 1-naphthylalanine, 3,3-diphenylalanine, p-fluorophenylalanine, or D-1,2,3,4-tetrahydroisoquinoline-3-carboxylic acid or L-1,2,3,4-tetrahydroiso-quinoline-3-carboxylic acid, etc.

The term "mutants" is readily understood by the skilled person. In particular, it refers to sequence variants, in which one or more of the amino acids as disclosed are changed, i.e. one or more amino acids are substituted by another one. Mutants of the invention preferably vary from a peptide of claim 1 by one, two, three or four amino acids. In a preferred embodiment, the mutations are conservative, such that the properties of the side chain of the changed amino acids do not vary substantially from the original amino acid. Mutants also include sequence variants, wherein one or more amino acids are deleted from the sequence or inserted into the sequence.

The term "fragments" is readily understood by the skilled person. In particular it refers to sequence variants in which the sequence is truncated at the N- or C-terminus. In preferred embodiments, the peptides lack up to 2, 4 or 6 amino acids at the N- and/or C-terminus.

The term "covalently linked oligomers" is readily understood by the skilled person. In particular it refers to multiple peptide chains covalently linked to each other. The peptide chains can have the identical or a different amino acid sequence. The covalent bond can be a direct bond between the respective peptide chains such as a disulfide bond, thioether bond, ether bond, amide bond. The peptide chains can also be covalently linked by a spacer of any chemical nature (Houben-Weyl, Methods of organic chemistry, Synthesis of peptides and peptidomimetics, Georg Thieme Verlag, Stuttgart 2002).

The term "derivative" is readily understood by the skilled person. In particular it refers to a chemically modified peptide. This modification could be a single amino acid substitution, multiple substitutions or different chemical modifications of the peptide at the N- and C-terminus, the side chains of the peptide, the C$\alpha$- and N$\alpha$-atoms of the peptide backbone, and the atoms forming the peptide bonds of the backbone.

The term "amidated" is readily understood by the skilled person. In particular it refers to a modification of a peptide in which the C-terminal carboxyl group is replaced by an $CONR_2$-group where R is a hydrogen atom or any functional group that can replace at least one of the hydrogen atoms.

The term "acylated" is readily understood by the skilled person. In particular it refers to peptides that contain a covalently linked carboxylic acid residue other than an amino acid at amino groups at the N-terminus and/or at side chains of amino groups.

The term "alkylated" is readily understood by the skilled person. In particular it refers to peptides which are modified with an alkyl group of various length and structure at the N-terminal amino group, at any backbone atom and/or at any functional group of a side chain.

The term "sulfated" is readily understood by the skilled person. In particular it refers to peptides carrying a sulfate moiety at the hydroxyl group of a tyrosine or substituted tyrosine derivative residue.

The term "pegylated" is readily understood by the skilled person. In particular it refers to peptides which contain covalently linked a polyethyleneglycol (PEG) moiety consisting of at least two repeating units —$CH_2$—$CH_2$—O— typical of polyethyleneglycol. Preferred is a so-called mini-PEG group. Pegyl groups may have a molecular weight of up to 20 KDa and can be bound to different functional groups in a peptide sequence directly or via a spacer group at the N- and/or C-terminus and/or side chain functional groups. The spacer group is selected from the group of bifunctional hydrocarbon chains characterised by a backbone of two, three, four, five, six, seven, eight or nine carbon atoms, and two functional groups, such as two amino groups, two carboxyl groups or one amino group and one carboxyl group. One or more pegyl groups can be contained at different sites of a peptide.

The term "phosphorylated" is readily understood by the skilled person. In particular it refers to peptides where the hydroxy groups of the side chains of threonine, serine, hydroproline, hydroxylysine, tyrosine, and/or any other non-natural hydroxy amino acid is esterified with a phosphate group.

The term "glycosylated" is readily understood by the skilled person. In particular it refers to peptides that contain a monomeric and/or oligomeric carbohydrate moiety which is linked via the glycosilic or an alcoholic hydroxy group to the side chains of serine, threonine, tyrosine, asparagine, and/or non-natural amino acids.

The term "cyclic" is readily understood by the skilled person. In particular it refers to peptides that contain a cyclic structural motif. The cyclization can be achieved by backbone cyclization or by linking a side chain of an amino acid to a side chain of a different amino acid present in the same molecule. In a preferred embodiment of the invention, two cysteine residues of a peptide or one carboxylic acid side chain and one amino group-containing side chain form a cyclic motif via a disulfide bond or an amide bond. The peptides VIR-161 (SEQ ID NO. 3), VIR-162 (SEQ ID NO. 4), VIR-163 (SEQ ID NO. 5), VIR-164 (SEQ ID NO. 6), VIR-165 (SEQ ID NO. 7), VIR-166 (SEQ ID NO. 8), VIR-272 (SEQ ID NO. 36), VIR-273 (SEQ ID NO. 37), VIR-274 (SEQ ID NO. 38), VIR-280 (SEQ ID NO. 39), VIR-344 (SEQ ID NO. 49), VIR-345 (SEQ ID NO. 50), VIR-346 (SEQ ID NO. 51), VIR-348 (SEQ ID NO. 52), VIR-350 (SEQ ID NO. 53), VIR-351 (SEQ ID NO. 54), VIR-352 (SEQ ID NO. 55), VIR-353 (SEQ ID NO. 56), VIR-354 (SEQ ID NO. 57), VIR-355 (SEQ ID NO. 58), VIR-356 (SEQ ID NO. 59), VIR-357 (SEQ ID NO. 60), VIR-358 (SEQ ID NO. 61), VIR-568 (SEQ ID NO. 84), VIR-570 (SEQ ID NO. 85), VIR-576 (SEQ ID NO. 86) all possess two cysteine residues and may adapt a cyclic form. These peptides may also occur as linear molecules. Preferred embodiments are the cyclic form of these peptides since they are characterised by a higher structural and biological stability.

Surprisingly, it was found that by specifically varying the amino acid sequence of VIRIP (SEQ ID NO. 1), peptides with a significantly increased activity against HIV were obtained. The most significant increase in activity is observed, when the L-proline at position 10 is substituted by a D-proline, and/or two cysteines are introduced at amino acid positions 6 and 11, and/or when the positively charged lysine at position 13 is exchanged against an amino acid with a hydrophobic or aromatic side chain. It is believed that the activity when compared to wild-type VIRIP (SEQ ID NO. 1) is increased due to a change in structure. Cysteine bridges are known to alter the structure and to reduce the flexibility of a peptide significantly, as well as the introduction of a D-proline, which causes a change in secondary structural elements of a peptide and thus a changed orientation of different parts of the peptide to each other. Furthermore, the exchange of a lysine against an uncharged hydrophobic or aromatic amino acid will alter the structure, because a possible interaction of the positively charged lysine side chain with the negatively charged amino acids at positions 2 and 11 of the same molecule, or with a negatively charged portion of a receptor molecule is changed.

A significant increase in the anti-HIV activity is further observed when the alanine residue at position 3 is exchanged to a positively or negatively charge residue by substitution with lysine or aspartic acid residues. The introduction of a charged residue at position 3 can enhance the binding strength to a corresponding part of a receptor molecule by increased electrostatic or dipolar forces. The exchange of the amino acid residues at positions 7 or/and 15 against a small amino acid residue, in particular glycine, has also been found to increase the anti-HIV activity. Glycine residues are the least sterically hindering residues and allow an optimal internal structural arrangement of a peptide when binding to a receptor molecule or when forming aggregates with themselves required for binding with a receptor molecule. The described substitutions may be combined in peptides of the invention. Furthermore, the antiviral activity is increased when peptides of the invention are homooligomerized, in particular homodimerized. A dimerization of peptides of the invention can be achieved chemically by covalent linking of two identical peptide chains. The covalent link can be a direct bond between side chain functional groups such as the thiol group of cysteine residues, or a bond involving a spacer between the peptide chains as is present when two identical chains of a peptide of the invention are bound to the two amino groups of a lysine residue. The latter is often referred to as the smallest form of a lysine-core dendrimer (Sadler K., J. Biotechnology, 2002, 90, 195-229). Oligomers, in particular dimers of peptides of the invention, can induce a structurally and/or biologically more stable form of the molecules. In addition, they can increase the local concentration of the antivirally active peptide at the site of action. They can thus provide forms of the peptides of the invention which interact more favourable with a receptor molecule.

Peptides according to the invention can be easily chemically synthesised or produced by recombinant expression. Due to the small size, i.e. the low number of amino acid the peptides of the invention are composed of, the entire peptide synthesis technologies can be utilised to chemically synthesise such substances. In comparison to the synthesis of the HIV fusion inhibitor T-20, which requires the synthesis of three individual fragments, and subsequently the joining of the three fragments to give rise to the final product T-20, the peptides of the present invention, can be synthesised at large scale by stepwise solid phase methods or by solution phase chemistry. Thus the manufacturing process of the peptides of the present invention is straightforward and therefore the costs of the goods comprising the peptides of the present invention are lower. A further advantage of the peptides of the present invention is their solubility and stability over a broad range of pH (pH 2-8.5) in solvents of different ionic strength.

The chemical synthesis can be carried out on a solid support using solid-phase technologies or in solution phase, both being standard methods known to the skilled person. Peptides according to the invention can also be synthesized by the ligation of two or more side chain-protected or side chain-unprotected fragments, standard methods known to the skilled person (Tam J. P., Biopolymers, 2001, 60, 194-205). The solid-phase synthesis of peptides according to the invention or its fragments can be carried out using the Fmoc/tBu- or Boc/Bzl-protection pattern of amino acids. Other protective groups that are not in the standard Fmoc-protection scheme can be used. Purification of synthetic peptides is achieved by chromatographic methods such as reverse-phase, ion exchange or size-exclusion. The chemical methods for the chemical synthesis of the peptides of the invention mentioned here are surveyed in several review publications (examples: Chan W. C. et al. (editors), Fmoc solid phase peptide synthesis: A practical approach, Oxford University Press, Oxford, 2000; Seewald N. et al., Peptides: biology and chemistry, Wiley-VCH, Weinheim, 2002; Goodman M., Houben-Weyl, Methods of organic chemistry, Synthesis of peptides and peptidomimetics, Georg Thieme Verlag, Stuttgart 2002).

The introduction of a disulfide bond into peptides of the invention may be achieved by applying oxidative chemical methods with peptides containing two cysteine residues known to the skilled person (Pennington et al. (editors), Peptide synthesis protocols, Humana Press, Totowa 1994; Chan W. C. et al. (editors), Fmoc solid phase peptide synthesis: A practical approach, Oxford University Press, Oxford, 2000). Disulfides of peptides of the invention may be generated from reduced precursor peptides containing one or two unprotected cysteine residues obtained from solid-phase or solution synthesis by oxidative treatment. As oxidizing agents oxygen, dimethylsulfoxide, iron(III) salts, iodine, or others may be used. Disulfides of peptides of the invention may alternatively be introduced into the peptides from precursors containing protective groups at the corresponding cysteine residues. As protective groups acetamidomethyl, tert-butyl, S-tert-butyl or others may be used. Cleavage of protective groups and intra-chain disulfide bond formation may be carried out using agents such as iodine, phosphines, or others.

Cyclic peptides other than those with a disulfide bond can be obtained via backbone cyclization of the peptide or via a chemical bond between at least one reactive side chain group such as amino, carboxy, hydroxy or thio and any other reactive group present in the same molecule, as known to the skilled person (Li et al., Curr. Top. Med. Chem., 2002, 2, 325-341; Tam J. P., Biopolymers, 2001, 60, 194-205; Goodman M., Houben-Weyl, Methods of organic chemistry, Synthesis of peptides and peptidomimetics, Geórg Thieme Verlag, Stuttgart 2002).

Covalently linked oligomers of peptides are obtained by linking two peptide chains via different types of chemical bonds. Disulfide-linked oligomers are synthesized by coupling the two peptide chains either via activated cysteines or without any preactivation of the cysteines (Sacca B. et al., J. Pept. Sci., 2002, 8, 192-204; Seewald N. et al., Peptides: biology and chemistry, Wiley-VCH, Weinheim, 2002). Thioether bonds and ether bonds and peptide bonds between two peptide chains can be introduced according to different methods known to the skilled person and described in the literature (Seewald N. et al., Peptides: biology and chemistry, Wiley-VCH, Weinheim, 2002). Lysine-core dendrimers can be synthesized by coupling Fmoc-Lys(Fmoc)-OH to a solid support. After deprotection of the amino acid solid phase peptide synthesis leads to the oligomeric peptides (Seewald N. et al., Peptides: biology and chemistry, Wiley-VCH, Weinheim, 2002; Chan W. C. (editors) Fmoc solid phase peptide synthesis: A practical approach, Oxford University Press, Oxford 2000). Lysine can be replaced by any other amino acid containing two amino groups.

Amidated peptides are obtained by solid phase peptide synthesis using resins carrying an amide linker on which the peptide chain is assembled. Acid cleavage of correspondingly synthesized peptides results in peptide amides. In solution phase synthesis amidated peptides are obtained when the C-terminal amino acid is used as a building block which has a preformed carboxamide at the C-terminus. (Chan W. C. (editors) Fmoc solid phase peptide synthesis: A practical approach, Oxford University Press, Oxford 2000).

Acylated peptides are obtained by the skilled person through converting a peptide with free amino or hydroxy groups using activated acylation reagents derived from carboxylic acids such as acyl halogenides or carboxylic anhydride or other reactive carbonyl compounds to a corresponding acylated peptide. As an alternative, acelytion can be achieved using free carboxylic acids which are activated in situ by phosphonium- or uronium-type compounds (Greene T. W., Protective groups in organic chemistry, John Wiley & Sons, New York, 1991; Kocienski P., Protecting groups, Thieme-Verlag, Stuttgart 1994).

Alkylated peptides may be obtained by incorporating pre-alkylated amino acid building blocks when carrying out peptide synthesis on the solid support or in solution. Such amino acids are coupled onto the peptide chains using standard activation protocols known to the skilled person (Chan W. C. (editors) Fmoc solid phase peptide synthesis: A practical approach, Oxford University Press, Oxford 2000). Alkylation may also be achieved after assembly of a peptide chain by using appropriate alkylation methods known to the skilled person (Greene T. W., Protective groups in organic chemistry, John Wiley & Sons, New York, 1991; Kocienski P., Protecting groups, Thieme-Verlag, Stuttgart 1994). Such methods may be applied to reactive groups such as amino, hydroxy, thio and peptide bonds of the peptide backbone in a partially protected peptide. Sulfated peptides are obtained by using presulfated building blocks of tyrosine or tyrosine derivatives in solid phase or solution peptide synthesis. O-sulfates remain attached to the hydroxy group during peptide cleavage from the resin when highly acid-labile resins such as 2-chlorotrityl resin are used for synthesis (Seewald N. et al., Peptides: biology and chemistry, Wiley-VCH, Weinheim, 2002).

Pegylated peptides contain pegyl residues bound to functional groups of a peptide. Pegyl residues are characterized as hydrophilic linear or branched polymeric chains with a repeating unit —$CH_2$—$CH_2O$—. Pegyl residues are introduced into a peptide after assembly of the peptide chain using suitable functionally modified and reactive pegyl-containing substances. Various activated pegyl groups can be attached by the skilled person to peptides by different activation methods to different side chains or terminal functional groups of a peptide such as amino, carboxyl, hydroxy and thio (Veronese F. M. et al., Bioconjug. Chem., 2001, 12, 62-70; Veronese F. M., Biomaterials, 2001, 22, 405-417).

Phosphorylated peptides can be synthesized by solid phase or solution phase peptide synthesis. Synthesis of phosphorylated peptides is usually achieved by the skilled person utilizing phosphorylated hydroxy amino acid building blocks and/or by post-chain assembly phosphorylation of protected peptides with one or more free hydroxy functional groups (Murray J. S., Biopolymers; 2001, 60, 3-31; Chan W. C. et al. (editors), Fmoc solid phase peptide synthesis: A practical approach, Oxford University Press, Oxford, 2000; Seewald N. et al., Peptides: biology and chemistry, Wiley-VCH, Weinheim, 2002).

Glycosylated peptides can be obtained by the skilled person using glycosylated amino acid building blocks which can be incorporated into solid phase or solution phase synthesis of peptides or by the global post-chain assembly glycosylation approach (Davis B. G., Chem. Rev., 2002, 102, 579-602; Chan W. C. et al. (editors), Fmoc solid phase peptide synthesis: A practical approach, Oxford University Press, Oxford, 2000; Seewald N. et al., Peptides: biology and chemistry, Wiley-VCH, Weinheim, 2002).

The invention also relates to nucleic acids coding for peptides of the invention. Preferred nucleic acids are DNA and RNA, especially cDNA and mRNA.

Subject of the invention are also antibodies specifically binding to peptides of the invention. The term "specifically" is readily understood by the skilled person. In particular, it means that the antibodies do not bind or do essentially not bind related peptides like VIRIP which are not peptides of the invention. A person skilled in the art obtains antibodies against peptides of the invention by routine methods, and will select specific antibodies of the invention by known screening methods.

The invention relates to peptides which specifically interact with and bind to the N-terminal region of the envelope protein gp41 of HIV. The term "interact with" and "bind to" is readily understood by the skilled person. By such binding and interaction, peptides of the invention block infection of host cells by HIV particles. The present invention also relates to peptides which bind to synthetic peptides corresponding to the fusion peptide of gp41 of HIV. A person skilled in the art detects binding and interaction of peptides of the invention to the synthetic fusion peptide of gp41 of HIV by applying quantitative structure/activity relationship (QSAR) assays. These assays comprise but are not limited to the detection of the suppression of the hemolytic effect of the synthetic fusion peptide (Mobley P. W. et al., Biochim. Biophys. Acta, 1992, 1139, 251-256; Gordon L., Biochim. Biophys. Acta, 1992, 1139, 257-274), microcalorimetry (Gohike H. et al., Angew. Chem. Int. Ed. Engl., 2002, 41, 2644-2676), or NMR-spectroscopical techniques which can be chemical shift titration experiments or saturation transfer difference spectroscopy (Meyer et al., Ernst Schering Res. Found. Workshop, 2004, 44, 149-167).

The invention also relates to a medicament containing the peptides, nucleic acids or antibodies of the invention. The medicament is preferably provided in galenic formulations for oral, intravenous, intramuscular, intracutaneous, subcutaneous, intrathecal administration, or as an aerosol for transpulmonary administration.

In a preferred embodiment, the medicament comprises at least one further therapeutic agent. Said at least one further therapeutic agent can be a viral protease inhibitor, a reverse transcriptase inhibitor, a fusion inhibitor, a cytokine, a cytokine inhibitor, a glycosylation inhibitor or a viral mRNA inhibitor, etc. Preferably, such inhibitors are directed against HIV. Such combined therapeutics are highly relevant in the treatment of AIDS. The peptides, nucleic acids and antibodies of the invention are preferably used in manufacturing of a medicament for the treatment of HIV infections. This comprises all known strains of the retrovirus HIV (human immunodeficiency virus), especially the most common strains of HIV-1. HIV-1 is associated with the outbreak of AIDS.

The invention also relates to a diagnostic agent containing peptides, nucleic acids or antibodies of the invention. The diagnostic agent may be used for assay systems for testing isolated plasma, serum, tissue, urine and cerebrospinal fluid levels for HIV infections.

The invention also relates to assay systems which involve peptides of the invention as a tool to identify substances which bind to the envelope protein gp41 of HIV, in particular the N-terminal fusion peptide of gp41. Such assays can be any system which is suitable to measure the binding of any substance to the fusion peptide either integrated in the entire gp41 protein in isolated, viral, or any other form, or in synthetic form with a length up to 35 amino acid residues starting with the very N-terminus of gp41. In such assays, which can be any spectroscopical, cellular, or radio-ligand assay, the binding of a substance in competition to peptides of the invention is measured. As a result of such competition assays using peptides of the invention as a tool, the identification of substances with increased affinity and binding site specificity to HIV gp41 is achieved. Such substances have an improved potency to block cellular infection by HIV particles. They can be used as improved therapeutic agents to cure AIDS.

Figure 2:
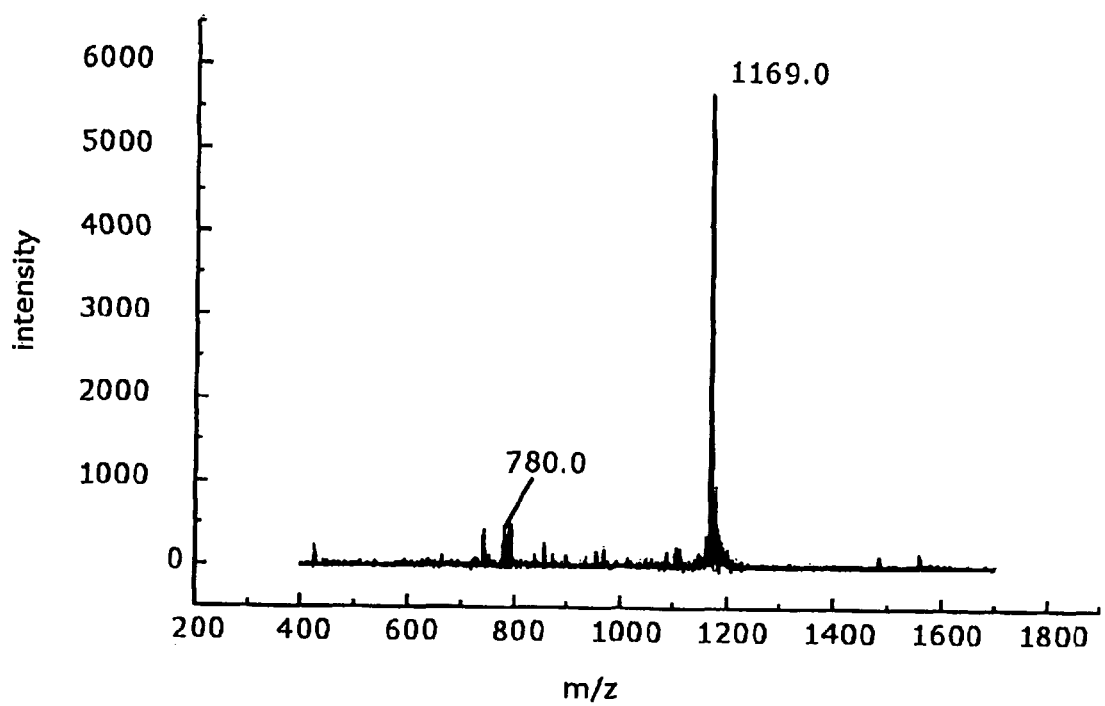
FIG. 2: Electrospray-ionization mass spectrum (ESI-MS) of purified VIR-199 (sequence: LEAIPMSIPpEFLFNK-PFVF) (SEQ ID NO. 18). The mass spectrum was recorded using a Sciex API 100 mass spectrometer. The molecular ions for $[M+2H]^{2+}$ (m/z 1169.0) and $[M+3H]^{3+}$ (m/z 780.0) are indicated.
Figure 3:
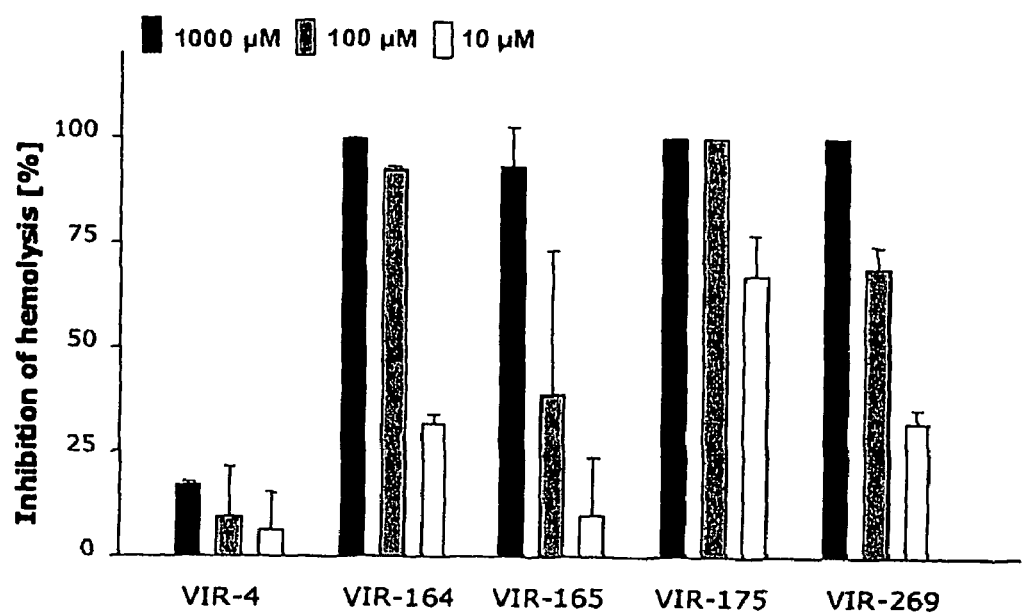
FIG. 3: Dose dependent inhibition of fusion peptide hemolysis by various VIRIP peptides. The peptides (VIRIP (SEQ ID NO. 1), VIR-164 (SEQ ID NO. 6), VIR-165 (SEQ ID NO. 7), VIR-175 (SEQ ID NO. 10), VIR-269 (SEQ ID NO. 35) at 1000 μM, 100 μM and 10 μM were preincubated with 100 μM fusion peptide and the hemoglobin release in human erythrocytes was measured. The Y-axis reflects the inhibition of the fusion peptide-induced hemolysis depending of the concentration of peptides. The extent of inhibition of hemolysis is thus a measure for the binding of peptides to the fusion peptide. Peptides that exhibit lower $IC_{50}$ values than VIRIP inhibit more effectively infection of cells compared to VIRIP.
Figure 4:
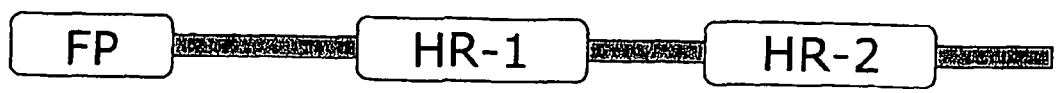
FIG. 4: Schematic drawing of gp41. The three domains, the fusion peptide (FP) domain, the HR-1 and HR-2 domains are indicated. The fusion peptide is located at the N-terminus of gp41.

After synthesis of the various peptides of the present invention, yields were examined. For all peptides good yields were achieved (see table 1), reflecting the ease of the synthesis process. The peptides of the present invention were subjected to various tests.

First, human cells were exposed to the peptides of the present invention in order to test their cytotoxicity. All peptides that were tested, namely VIR-161 (SEQ ID NO. 3), VIR-162 (SEQ ID NO. 4), VIR-163 (SEQ ID NO. 5), VIR-164 (SEQ ID NO. 6), VIR-165 (SEQ ID NO. 7), VIR-166 (SEQ ID NO. 8), VIR-170 (SEQ ID NO. 9), VIR-175 (SEQ ID NO. 10), VIR-182 (SEQ ID NO. 11), VIR-184 (SEQ ID NO. 12), VIR-190 (SEQ ID NO. 13), VIR-191 (SEQ ID NO. 14), VIR-192 (SEQ ID NO. 15), VIR-193 (SEQ ID NO. 16), VIR-197 (SEQ ID NO. 17), VIR-199 (SEQ ID NO. 18), VIR-229 (SEQ ID NO. 19), VIR-234 (SEQ ID NO. 20), VIR-243 (SEQ ID NO. 21), VIR-252 (SEQ ID NO. 22), VIR-255 (SEQ ID NO. 23), VIR-257 (SEQ ID NO. 24), VIR-258 (SEQ ID NO. 25), VIR-259 (SEQ ID NO. 26), VIR-260 (SEQ ID NO. 27), VIR-261 (SEQ ID NO. 28), VIR-262 (SEQ ID NO. 29), VIR-263 (SEQ ID NO. 30), VIR-264 (SEQ ID NO. 31), VIR-265 (SEQ ID NO. 32), VIR-266 (SEQ ID NO. 33), VIR-268 (SEQ ID NO. 34), VIR-269 (SEQ ID NO. 35) were free of any cytotoxic effect. These data strongly suggest, that also those peptides not tested yet are non-cytotoxic.

The second set of experiments concerned the efficacy of the peptides of the present invention to inhibit HIV infection (see table 2). The peptides were tested on two HIV-1 strains and $IC_{50}$ values were calculated. The most active peptides had an $IC_{50}$ of equal or below 800 nM, whereby for example VIR-484 (SEQ ID NO. 79) had an $IC_{50}$ of 100 nM. Peptides with still considerable activity where those with an $IC_{50}$ of equal or below 2000 nM, and those with an $IC_{50}$ of equal or below 6500 nM still had an increased activity in comparison to the native VIRIP (SEQ ID NO. 1); the native VIRIP (SEQ ID NO. 1) was found to have an $IC_{50}$ of 15,000 or 22,000, if tested with HIV strains NL4-3 or DTV, respectively. To summarise table 2, the peptides of the present invention displayed a 4-fold to 161-fold increase in anti-HIV activity in comparison to the native VIRIP.

The third set of experiments determined the in vivo toxicity of the VIRIP peptides of the present invention. Considering the positive outcome of the in vitro cytotoxicity test, it was sufficient to test only one compound. Mice were injected with VIR-121 (SEQ ID NO. 2), observed over a period before sacrificing them. Throughout the life of the mice no signs of reduced or increased motility, dyspnea, ataxia, nor a reduced or increased muscle tone were observed. No changes of behaviour were observed, and behaviour was comparable to that of the control animals. The pathological examination did not reveal any abnormalities. It was therefore concluded that the peptides of the present invention are well tolerated by a living organism.

A forth set of experiments concerned the stability of the peptides of the present invention in mammalian plasma (see table 3). Plasma isolated from various animals and humans was spiked with defined amounts of various peptides of the present invention. The peptides displayed a considerable half life in human plasma, most prominent being VIR-512 (SEQ ID NO. 83), VIR-580 (SEQ ID NO. 87) and VIR-357 (SEQ ID NO. 60), with a half-life of 315 h, 38.9 h and 23.3 h, respectively. These peptides also showed considerable stability in the animal plasma, but the actual values varied from those found for human plasma. The native VIRIP (SEQ ID NO. 1) has a half-life of 53.7 h in human plasma. The results also showed, that rat plasma is not a suitable model system for these type of experiments.

In the final set of experiments the ability of peptides of the invention to interact with the fusion peptide of gp41 by measuring the suppression of the fusion peptide-induced hemolysis upon addition of increasing doses of peptides of the invention was tested. All peptides tested were more efficient in inhibiting the hemolytic effect of the fusion peptide than the native VIRIP. It was concluded that peptides of the invention change structural properties of the fusion peptide by specific interaction.

In essence, the peptides of the present invention are characterised by their anti-HIV activity, which, expressed as $IC_{50}$, is equal to or below 6500 nM, whereby the most active peptides have an $IC_{50}$ of below 800 nM. Individual peptides of the present invention were found to have $IC_{50}$ of below 100 nM (see table 1).

EXAMPLES

In total over 600 peptides were synthesised, of which only 84 are presented here in more detail (see table 1). Not every experiment was conducted with each peptide. Those 84 peptides presented here were more active against HIV as judged by their $IC_{50}$, than the remaining peptides. However, the 22 most active peptides of the group of 84 peptides were further selected, and subjected to an additional anti-viral activity test, using a different HIV strain. The most promising candidates of that screening were subjected to a plasma stability test. A detailed description of the performed experiments is given below.

Example 1

Chemical synthesis of Peptides of the Present Invention

The peptides according to the invention were chemically synthesized utilizing the principle of solid-phase peptide synthesis and the Fmoc or Boc protective group strategy (Atherton and Sheppard, 1989, Solid Phase Peptide Synthesis, IRL Press; Merrifield, 1986, Solid phase synthesis, Science 232, 341-347), but can also be synthesized with solution phase synthesis or by coupling protected or unprotected fragments of the peptides according to the invention.

As an example, the synthesis of the peptide VIR-199 (amino acid sequence: LEAIPMSIPpEFLFNKPFVF) (SEQ ID NO. 18) is described here using fluorenylmethoxycarbonyl (Fmoc)-protected amino acids on an automated peptide synthesizer 433A (Applied Biosystems). The synthesis was performed using a preloaded Fmoc-Phe-Wang resin with a loading capacity of 1 mmol/g resin with standard HBTU [(2-(1H-benzotriazol-1-yl)-1,1,3,3-tetramethyluronium-hexafluorophosphate]/HOBt (1-hydroxybenzotriazol) activation with capping cycles using acetic anhydride in N-methylpyrrolidinone (NMP) at a scale of 0.2 mmol. The side chains of the amino acid building blocks used were protected as follows: Glu(OtBu), Ser(tBu), Lys(Boc), Asn(Trt). Acylation steps for peptide chain assembly were carried out for 15-60 min, and Fmoc groups were deprotected with piperidine in NMP after each acylation. After deprotection of the leucine residue at position 1, the resulting protected peptidyl resin was washed with NMP, 2-propanol and dichloromethane and dried. The dry resin was treated at room temperature with a fresh mixture of trifluoracetic acid/ethanedithiole/water (94:3:3, vol/vol/vol, 40 ml/g resin) for 2-4.5 h. The mixture was filtrated into ice-cold tert-butylmethylether (TBME) to facilitate precipitation of the peptide. The resulting precipitate was separated by centrifugation, washed with TBME and dried under vacuum. The crude peptide was dissolved in diluted acetic acid and loaded onto a preparative Vydac C18 column (47×300 mm, 15-20 μm, flow rate 40 ml/min; solvent A, 0.07 volume % TFA; solvent B, 0.07 volume % TFA in acetonitrile/$H_2O$ 80:20 (volume %); UV detection at 215 nm; with the following gradient: 45-70 volume % B in 50 min. The fractions containing the desired pure peptide, as detected by mass spectrometry (API 100, Perkin Elmer) and analytical C18 HPLC or, alternatively, capillary zone electrophoresis, were pooled and dried by lyophilization. The lyophilized peptide was used for analysis of purity and molecular weight by analytical C18 HPLC (FIG. 1), capillary zone electrophoresis, and mass spectrometry (FIG. 2). The yield of the peptide LEAIPMSIPpEFLFNK-PFVF (SEQ ID NO. 18) was 138 mg.

The process for synthesis of the peptides according to the invention was adapted to larger scales ranging from 0.5 to 20 mmol yielding purified peptides of the present invention in amounts between 1 g and 5 g. The synthesis process was also adapted to small-scale multiple peptide synthesis.

Peptides according to the invention having intramolecular disulfide bonds were treated with air at pH 7.5-8.5, with or without dimethylsulfoxide, or alternatively, from linear precursors with two acetamidomethyl-protected cysteine residues by iodine oxidation to facilitate cysteine bridge formation. Using these general synthetic approaches, the following peptides, among others, were synthesized, purified by chromatographic methods to a degree of up to 98% and analysed:

TABLE 1

Yields and molecular weight of synthetic peptides. Yields are obtained from synthesis at various scales.

| Peptide | Yield [mg] | Molecular weight (calculated) | Molecular weight (determined by mass spectrometry) |
| --- | --- | --- | --- |
| VIR-121 | 109 | 2246.7 | 2246.5 |
| VIR-161 | 34 | 2190.6 | 2190.3 |
| VIR-162 | 56 | 2119.6 | 2119.0 |
| VIR-163 | 98 | 2232.7 | 2232.8 |
| VIR-164 | 35 | 2266.7 | 2266.5 |
| VIR-165 | 72 | 2238.7 | 2238.0 |
| VIR-166 | 37 | 2361.4 | 2362.3 |
| VIR-170 | 50 | 2265.7 | 2267.0 |
| VIR-175 | 105 | 2279.7 | 2279.5 |
| VIR-182 | 56 | 2217.6 | 2217.2 |
| VIR-184 | 82 | 2260.7 | 2260.4 |
| VIR-190 | 71 | 2175.6 | 2175.2 |
| VIR-191 | 25 | 2231.7 | 2231.8 |
| VIR-192 | 53 | 2265.7 | 2265.0 |
| VIR-193 | 138 | 2294.7 | 2295.0 |
| VIR-197 | 50 | 2322.7 | 2322.3 |
| VIR-199 | 138 | 2336.8 | 2336.5 |
| VIR-229 | 58 | 2228.6 | 2228.3 |
| VIR-234 | 78 | 2216.6 | 2217.0 |
| VIR-243 | 34 | 2312.7 | 2312.7 |
| VIR-252 | 142 | 2290.7 | 2290.3 |
| VIR-255 | 56 | 2303.7 | 2303.5 |
| VIR-257 | 151 | 2329.0 | 2328.2 |
| VIR-258 | 50 | 2345.0 | 2344.4 |
| VIR-259 | 110 | 2312.9 | 2312.4 |
| VIR-260 | 162 | 2324.0 | 2323.4 |
| VIR-261 | 79 | 2371.0 | 2370.3 |

TABLE 1-continued

Yields and molecular weight of synthetic peptides. Yields are obtained from synthesis at various scales.

| Peptide | Yield [mg] | Molecular weight (calculated) | Molecular weight (determined by mass spectrometry) |
| --- | --- | --- | --- |
| VIR-262 | 61 | 2234.6 | 2334.3 |
| VIR-263 | 147 | 2334.6 | 2334.3 |
| VIR-264 | 102 | 2379.1 | 2378.5 |
| VIR-265 | 118 | 2329.0 | 2330.0 |
| VIR-266 | 175 | 2361.8 | 2361.2 |
| VIR-268 | 123 | 2308.5 | 2308.3 |
| VIR-269 | 46 | 2301.0 | 2300.3 |
| VIR-272 | 44 | 2306.8 | 2306.5 |
| VIR-273 | 21 | 2340.8 | 2340.3 |
| VIR-274 | 24 | 2249.7 | 2249.0 |
| VIR-280 | 15 | 2223.7 | 2223.0 |
| VIR-284 | 34 | 2247.7 | 2247.3 |
| VIR-286 | 32 | 2199.7 | 2199.3 |
| VIR-290 | 44 | 2247.7 | 2247.3 |
| VIR-298 | 35 | 2343.8 | 2342.8 |
| VIR-320 | 37 | 2235.7 | 2235.3 |
| VIR-322 | 45 | 2292.8 | 2291.8 |
| VIR-323 | 44 | 2306.8 | 2306.3 |
| VIR-326 | 43 | 2260.7 | 2260.8 |
| VIR-328 | 49 | 2331.8 | 2331.8 |
| VIR-344 | 7 | 2209.8 | 2209.7 |
| VIR-345 | 19 | 2223.7 | 2223.0 |
| VIR-346 | 34 | 2161.6 | 2161.0 |
| VIR-348 | 5 | 2119.6 | 2119.0 |
| VIR-350 | 13 | 2211.7 | 2210.5 |
| VIR-351 | 32 | 2238.7 | 2238.5 |
| VIR-352 | 23 | 2266.8 | 2266.5 |
| VIR-353 | 17 | 2280.8 | 2280.0 |
| VIR-354 | 26 | 2190.7 | 2190.7 |
| VIR-355 | 18 | 2160.6 | 2160.0 |
| VIR-356 | 14 | 2256.7 | 2256.0 |
| VIR-357 | 26 | 2234.7 | 2234.3 |
| VIR-358 | 24 | 2247.7 | 2248.0 |
| VIR-376 | 53 | 2350.8 | 2350.3 |
| VIR-377 | 53 | 2336.8 | 2336.3 |
| VIR-380 | 46 | 2426.9 | 2427.0 |
| VIR-384 | 43 | 2408.9 | 2408.3 |
| VIR-396 | 38 | 2237.7 | 2237.0 |
| VIR-400 | 40 | 2313.8 | 2314.3 |
| VIR-416 | 36 | 2249.7 | 2249.3 |
| VIR-418 | 40 | 2306.8 | 2306.5 |
| VIR-445 | 30 | 2316.7 | 2316.8 |
| VIR-447 | 37 | 2290.6 | 2289.8 |
| VIR-448 | 31 | 2304.7 | 2304.3 |
| VIR-449 | 27 | 2304.7 | 2304.8 |
| VIR-452 | 28 | 2378.8 | 2378.3 |
| VIR-454 | 37 | 2391.8 | 2391.8 |
| VIR-455 | 25 | 2391.8 | 2391.8 |
| VIR-479 | 36 | 2332.8 | 2332.3 |
| VIR-483 | 35 | 2343.7 | 2344.0 |
| VIR-484 | 25 | 2343.7 | 2343.8 |
| VIR-485 | 42 | 2317.7 | 2317.8 |
| VIR-487 | 34 | 2330.7 | 2330.3 |
| VIR-488 | 36 | 2304.6 | 2304.5 |
| VIR-512 | 37 | 2293.6 | 2293.3 |
| VIR-568 | 13 | 2257.7 | 2257.3 |
| VIR-570 | 21 | 2205.6 | 2205.3 |
| VIR-576* | 12 | 4501.4 | 4502.0 |
| VIR-580 | 41 | 2569.2 | 2568.5 |
| VIR-590 | 41 | 2321.6 | 2320.8 |
| VIRIP | 265 | 2303.8 | 2303.6 |

*VIR-576 is a homo-dimer; an intermolecular disulfide bridge occurs at the cysteine at amino acid position 6.

Example 2

Cytotoxicity of the Peptides of Present Invention on Human Cells

The cytotoxicity of peptides of the invention was tested by evaluating the viability of human monocytic THP-1 cells. Cytotoxic effects of the peptides were tested by their influence on metabolic activity by means of the WST-1 assay (Roche Diagnostics, Germany). THP-1 cells were incubated with test peptides in a 96-well plate (approx. 25,000 cells per well) for 24 hours in RPMI-1640 medium containing 25 mM L-glutamine and 10 volume % fetal calf serum at 37° C. in an atmosphere with 5 volume % $CO_2$. Ten μl of a WST-1 solution was added to each cavity, and incubation of THP-1 cells was allowed for 2 further hours at corresponding conditions. Metabolically active THP-1 cells reduce WST-1, a light red tetrazolium salt, yielding a soluble yellow formazan salt. The amount of reduced WST-1 correlates directly to the number of living cells, and is measured photometrically at a wavelength of $\lambda$=450 nm using a microtiter plate reader (reference wavelength is 630 nm). As a positive control, the known cytotoxic substance cycloheximide was used at a concentration of 50 μg/ml; the cytotoxicity of cycloheximide was set to 100%. As another positive control the peptide MBI-28, a highly cytotoxic peptide known to the skilled person, was used with a maximum concentration of 300 μg/mL. As a negative control, cultured THP-1 cells not treated with the peptides of the invention or a positive control were used. The cytotoxicity of VIRIP peptides was calculated using the formula Viability [%]=[$A_{450\,nm}$ (peptide)–$A_{450\,nm}$ (cycloheximide)]/[$A_{450\,nm}$ (negative control)–$A_{450\,nm}$ (cycloheximide)]*100 and was correlated to the averaged viability of untreated THP-1 cells. The experiments were carried out at concentrations of peptides according to the invention of 30 μg/mL, 100 μg/mL, 300 μg/mL and 1000 μg/mL. The peptides VIR-161 (SEQ ID NO. 3), VIR-162 (SEQ ID NO. 4), VIR-163 (SEQ ID NO. 5), VIR-164 (SEQ ID NO. 6), VIR-165 (SEQ ID NO. 7), VIR-166 (SEQ ID NO. 8), VIR-170 (SEQ ID NO. 9), VIR-175 (SEQ ID NO. 10), VIR-182 (SEQ ID NO. 11), VIR-184 (SEQ ID NO. 12), VIR-190 (SEQ ID NO. 13), VIR-191 (SEQ ID NO. 14), VIR-192 (SEQ ID NO. 15), VIR-193 (SEQ ID NO. 16), VIR-197 (SEQ ID NO. 17), VIR-199 (SEQ ID NO. 18), VIR-229 (SEQ ID NO. 19), VIR-234 (SEQ ID NO. 20), VIR-243 (SEQ ID NO. 21), VIR-252 (SEQ ID NO. 22), VIR-255 (SEQ ID NO. 23), VIR-257 (SEQ ID NO. 24), VIR-258 (SEQ ID NO. 25), VIR-259 (SEQ ID NO. 26), VIR-260 (SEQ ID NO. 27), VIR-261 (SEQ ID NO. 28), VIR-262 (SEQ ID NO. 29), VIR-263 (SEQ ID NO. 30), VIR-264 (SEQ ID NO. 31), VIR-265 (SEQ ID NO. 32), VIR-266 (SEQ ID NO. 33), VIR-268 (SEQ ID NO. 34), VIR-269 (SEQ ID NO. 35), were tested. These peptides did not exhibit a cytotoxic effect on monocytic THP-1 cells compared to the positive controls cycloheximid and MBI-28.

Example 3

Inhibition of the HIV infection by the Peptides of Present Invention

P4-CCR5 indicator cells (Charneau et al., 1994; Journal of Molecular Biology 241, 651-662) expressing the primary CD4 receptor and both major HIV-1 entry cofactors CXCR4 and CCR5, were used to evaluate whether peptides according to the invention are potent inhibitors of HIV-1 infection. These cells contain the β-galactosidase reporter gene under the control of the HIV-1 promoter. Thus, activation of the β-galactosidase reporter gene allows to measure the efficiency of HIV-1 infection and thus to quantitate the potency of HIV-1 inhibitors (Detheux M. et al., 2000; Journal of Experimental Medicine 192, 1501-1508; Münch et al., 2002; Antimicrobial Agents and Chemotherapy 46, 982-990).

To perform a typical infection assay, P4-CCR5 cells (Charneau et al., 1994; Journal of Molecular Biology 241, 651-662; Charneau et al., Virology. 1994 205, 247-53) were kept in RPMI 1640 medium supplemented with 10 volume % FCS. This cell line coexpresses CD4 and both HIV-1 coreceptors CCR5 and CXCR4 and contains the β-galactosidase gene under the control of the HIV-1 promoter. Virus stocks were generated by the calcium coprecipitation method as described (Detheux et al., J Exp Med. 192:1501-8; 2000), and the p24 antigen levels were quantitated with an HIV p24 ELISA kit obtained through the NIH AIDS Reagent Program. Cells were seeded in flat-bottomed 96-well dishes, cultured overnight, and incubated with the different doses of peptide for 2 h before infection with virus containing 1 ng of p24 antigen in a total volume of 50 ml of medium. After overnight incubation, cells were washed twice and cultivated in fresh culture medium without inhibitory peptide. Three days after infection the cells were lysed, and infectivity was quantitated using the Galacto-Light Plus™ chemiluminescence reporter assay kit (Tropix, Bedford, Mass.) as recommended by the manufacturer. All infections were performed in quintuplicate.

The results of this assay demonstrate that peptides according to the invention have greatly enhanced anti-HIV-1 activity as compared to VIRIP. Peptides of the invention inhibited the infection by the X4-tropic HIV-1 NL4-3 and the HIV-1 NL4-3 DTV (from hereon called DTV)—DTV is a variant of NL4-3 and was originally described by Rimsky et al. (Journal of Virology 72, 986-993; 1998) as r4—molecular clones with more than 10-fold up to more than 100-fold higher efficiency than the original VIRIP. Peptides of the invention were also active against infection by the R5-tropic HIV-1 YU-2 molecular clone. These data demonstrate that the specific modifications of VIRIP greatly enhance the anti-HIV-1 potency of peptides according to the invention. Below, the $IC_{50}$ values of peptides of the invention obtained from the described infection assay are provided.

TABLE 2

Amino acid sequence and anti-HIV activity

| Peptide | Amino acid sequence | SEQ ID NO. | IC50 NL4-3 [nM] | IC50 DTV [nM] |
|---|---|---|---|---|
| VIR-121 | LEAIPMSIPpEVAFNKPFVF | 2 | 370 | 1790 |
| VIR-161 | LEAIPCSIPpCVAFNKPFVF | 3 | 550 | 570 |

TABLE 2-continued

Amino acid sequence and anti-HIV activity

| Peptide | Amino acid sequence | SEQ ID NO. | IC50 NL4-3 [nM] | IC50 DTV [nM] |
|---|---|---|---|---|
| VIR-162 | LEAIPCSIPPCVGFGKPFVF | 4 | 660 | 950 |
| VIR-163 | LEAIPCSIPPCVLFNKPFVF | 5 | 760 | 290 |
| VIR-164 | LEAIPCSIPPCVFFNKPFVF | 6 | 340 | 370 |
| VIR-165 | LEAIPCSIPPCFAFNKPFVF | 7 | 270 | 140 |
| VIR-166 | LEAIPCSIPPCVA(D-Tic)NKP(D-Tic)FVF | 8 | 356 | 506 |
| VIR-170 | LEAIPMSIPPEVFFGKPFVF | 9 | 1520 | 2000 |
| VIR-175 | LEAIPMSIPPEFLFGKPFVF | 10 | 225 | 300 |
| VIR-182 | LEAIPMSIPPELAFAKPFVF | 11 | 2250 | 2970 |
| VIR-184 | LEAIPMSIPPEIAFNKPFVF | 12 | 1990 | 5390 |
| VIR-190 | LEAIPMSIPpEVGFGKPFVF | 13 | 1840 | 3110 |
| VIR-191 | LEAIPMSIPpEVLFGKPFVF | 14 | 1790 | 560 |
| VIR-192 | LEAIPMSIPpEVFFGKPFVF | 15 | 1540 | 1210 |
| VIR-193 | LEAIPMSIPpEFAFNKPFVF | 16 | 1740 | 1380 |
| VIR-197 | LEAIPMSIPpEVFFNKPFVF | 17 | 1270 | 1440 |
| VIR-199 | LEAIPMSIPpEFLFNKPFVF | 18 | 2140 | 1650 |
| VIR-229 | LEAIPISIPpEVAFNKPFVF | 19 | 1280 | 2260 |
| VIR-234 | LEAIPMIGIPpEVAFNKPFVF | 20 | 740 | 6410 |
| VIR-243 | LEAIPMSIPPEFAFNKDFVF | 21 | 2160 | 1980 |
| VIR-252 | LEDIPMSIPpEVAFNKPFVF | 22 | 1750 | 1870 |
| VIR-255 | LEKIPMSIPpEVAFNKPFVF | 23 | 650 | 1230 |
| VIR-257 | LEAIPMSIPpEV(cyclohexylalanine)FNKPFVF | 24 | 860 | 660 |
| VIR-258 | LEAIPMSIPpE(1-naphthylalanine)AFNKPFVF | 25 | 640 | 620 |
| VIR-259 | LEAIPMSIPpE(p-fluorophenylalanine)AFNKPFVF | 26 | 860 | 1030 |
| VIR-260 | LEAIPMSIPpEV(4-pyridylalanine)FNKPFVF | 27 | 2150 | 2380 |
| VIR-261 | LEAIPMSIPpE(3,3-diphenylalanine)AFNKPFVF | 28 | 538 | 1029 |
| VIR-262 | LEAIPMSIPpEV(D-Tic)FNKPFVF | 29 | 940 | 580 |
| VIR-263 | LEAIPMSIPpEV(L-Tic)FNKPFVF | 30 | 770 | 330 |
| VIR-264 | LEAIPMSIPpEV(3-benzothienylalanine)FNKPFVF | 31 | 590 | 700 |
| VIR-265 | LEAIPMSIPpEV(3-thienylalanine)FNKPFVF | 32 | 1290 | 2210 |
| VIR-266 | LEAIPMSIPpEVWFNKPFVF | 33 | 590 | 830 |
| VIR-268 | LEAIPMSIPpEVAFNK(L-Tic)FVF | 34 | 1730 | 1480 |
| VIR-269 | LEAIPMSIPpEVAFNK(Oic)FVF | 35 | 2610 | 900 |
| VIR-272 | LEAIPMCIPPECLFNKPFVF | 36 | 999 | |
| VIR-273 | LEAIPMCIPPECFFNKPFVF | 37 | 332 | 1102 |
| VIR-274 | LEAIPMCIPPECLFGKPFVF | 38 | 576 | 1421 |
| VIR-280 | LEAIPCSIPPCFLFGKPFVF | 39 | 93 | |
| VIR-284 | LEAIPISIPPEVFFGKPFVF | 40 | 281 | |
| VIR-286 | LEAIPISIPPELAFAKPFVF | 41 | 559 | |
| VIR-290 | LEAIPISIPpEVFFGKPFVF | 42 | 562 | |
| VIR-298 | LEAIPISIPpEVWFNKPFVF | 43 | 969 | |
| VIR-320 | LEAIPMGIPpEVFFGKPFVF | 44 | 277 | |
| VIR-322 | LEAIPMGIPpEVFFNKPFVF | 45 | 836 | |
| VIR-323 | LEAIPMGIPpEFLFNKPFVF | 46 | 924 | |
| VIR-326 | LEDIPMGIPpEVAFNKPFVF | 47 | 963 | |
| VIR-328 | LEAIPMGIPpEVWFNKPFVF | 48 | 685 | |
| VIR-344 | LEAIPCSIPPCVFFGKPFVF | 49 | 348 | 448 |
| VIR-345 | LEAIPCSIPPCFLFGKPFVF | 50 | 298 | 376 |
| VIR-346 | LEAIPCSIPPCLAFAKPFVF | 51 | 541 | |
| VIR-348 | LEAIPCSIPpCVGFGKPFVF | 52 | 326 | 541 |
| VIR-350 | LEAIPCSIPpCVFFGKPFVF | 53 | 198 | |
| VIR-351 | LEAIPCSIPpCFAFNKPFVF | 54 | 203 | |
| VIR-352 | LEAIPCSIPpCVFFNKPFVF | 55 | 340 | 624 |
| VIR-353 | LEAIPCSIPpCFLFNKPFVF | 56 | 225 | 181 |
| VIR-354 | LEAIPCSIPpCVAFNKPFVF | 57 | 619 | |
| VIR-355 | LEAIPCGIPpCVAFNKPFVF | 58 | 582 | |
| VIR-356 | LEAIPCSIPPCFAFNKDFVF | 59 | 700 | |
| VIR-357 | LEDIPCSIPpCVAFNKPFVF | 60 | 497 | 704 |
| VIR-358 | LEKIPCSIPpCVAFNKPFVF | 61 | 706 | 944 |
| VIR-376 | LEAIPMSIPpEFLFGKPAFVF | 62 | 568 | |
| VIR-377 | LEAIPMSIPpEFLFGKPGFVF | 63 | 487 | |
| VIR-380 | LEAIPMSIPpEFLFGKPFFVF | 64 | 540 | |
| VIR-384 | LEAIPMSIPpEFLFGKPEFVF | 65 | 622 | |
| VIR-396 | LEAIPMSAPpEFLFGKPFVF | 66 | 628 | |
| VIR-400 | LEAIPMSFPpEFLFGKPFVF | 67 | 590 | |
| VIR-416 | LEAIPMGIPpEFLFGKPFVF | 68 | 369 | |
| VIR-418 | LEKIPMGIPpEFLFGKPFVF | 69 | 500 | |
| VIR-445 | LEAIPISIPpEV(D-Tic)FNKPFVF | 70 | 224 | |
| VIR-447 | LEAIPISIPpEVAFNK(L-Tic)FVF | 71 | 620 | |
| VIR-448 | LEAIPMGIPpEV(D-Tic)FNKPFVF | 72 | 318 | 325 |
| VIR-449 | LEAIPMGIPpEV(L-Tic)FNKPFVF | 73 | 274 | 240 |
| VIR-452 | LEDIPMSIPpEV(L-Tic)FNKPFVF | 74 | 184 | |
| VIR-454 | LEKPMSIPpEV(D-Tic)FNKPFVF | 75 | 464 | 1089 |
| VIR-455 | LEKPMSIPpEV(L-Tic)FNKPFVF | 76 | 134 | 353 |
| VIR-479 | LEDIPIGIPpEFLFNKPFVF | 77 | 479 | |

TABLE 2-continued

Amino acid sequence and anti-HIV activity

| Peptide | Amino acid sequence | SEQ ID NO. | IC50 NL4-3 [nM] | IC50 DTV [nM] |
|---|---|---|---|---|
| VIR-483 | LEKIPIGIPpEV(D-Tic)FNKPFVF | 78 | 765 | 866 |
| VIR-484 | LEKIPIGIPpEV(L-Tic)FNKPFVF | 79 | 100 | 339 |
| VIR-485 | LEKIPIGIPpEVAFNK(L-Tic)FVF | 80 | 760 | |
| VIR-487 | LEDIPIGIPpEV(L-Tic)FNKPFVF | 81 | 256 | |
| VIR-488 | LEDIPIGIPpEVAFNK(L-Tic)FVF | 82 | 415 | |
| VIR-512 | N-Me-LEAIPMSIPPEFLFGKPFVF | 83 | 138 | 615 |
| VIR-568 | LEAIPMSCPPEFCFGKPFVF | 84 | 367 | 552 |
| VIR-570 | LEAIPCSIPPECLFGKPFVF | 85 | 231 | |
| VIR-576* | (LEAIPCSIPPEFLFGKPFVF)$_2$ | 86 | 107 | 296 |
| VIR-580 | LEAIPMSIPPEFLFGKPFVF-miniPEG | 87 | 150 | 497 |
| VIR-590 | LEAIPMKIPPEFLFGKPFVF | 88 | 343 | |
| VIRIP | LEAIPMSIPPEVKFNKPFVF | 1 | 15000 | 22200 |

*VIR-576 is a homo-dimer; an intermolecular disulfide bridge occurs at the cysteine at amino acid position 6.

Example 4

Toxicity of the Peptides of the Present Invention in Mice

Acute toxicity was evaluated with VIR-121 (LEAIPM-SIPpEVAFNkPFVF) after a single intravenous injection into the tail vein of SCID-C.B 17-mice. A dose of 927 mg VIR-121 (SEQ ID NO. 2) dissolved in 13.6 ml 0.9 volume % sodium chloride solution per kg body weight (equivalent to 20.4 mg or 272 µL per mouse) was applied. Injection speed was dose within 15 seconds. Three animals were treated with the test substance, and the animals were observed at time points of 5, 15, 30 min, and 1, 3, 6, and 24 hours after administration of the sample into the tail vein. As a control, 3 mice were each treated with a corresponding volume of vehicle (0.9 volume % NaCl). After 24 hours, the animals were sacrificed, dissected and inspected macroscopically. During and after application until the end of the observation period of 24 hours for all animals treated with VIR-121 (SEQ ID NO. 2) no signs of reduced or increased motility, dyspnea, ataxia, nor a reduced or increased muscle tone were observed. No changes of behaviour was observed, and behaviour was comparable to that of the control animals. No findings were obtained from macroscopic necropsy compared to the control group.

Example 5

Stability of Peptides of the Invention in Mammalian Plasma

To evaluate the half-life and exposure of peptides of the invention, the stability of peptides was examined in mammalian plasma after incubation in EDTA plasma obtained from human, dog, cynomolgus and rat at 37° C. Plasma was spiked resulting in concentrations of 40 µg/ml and stored at 37° C. At time points 0, 15, 30, 45, 60, 120, 180, 240 and 300 min samples of 20 µl were taken. The plasma was immediately mixed for precipitation with the two-fold volume of acetonitrile containing 0.15% (w/v) n-nonyl-β-D-glucopyranoside. Following centrifugation the supernatants were mixed with the two-fold volume of 0.1% (v/v) trifluroacetic acid. Twenty µl of these solutions were analyzed by LC-MS. Chromatography was performed using a gradient with the following eluents: eluent A: water containing 0.06% trifluroacetic acid (v/v), eluent B: acetonitrile/water 80:20 (v/v; with 0.05% trifluoroacetic acid; v/v). A C18 precolumn was used in combination with a C18 separation column (300 Å, 5 µm, 150×1 mm inner diameter) at a flow rate of 30 µl/min. HPLC eluates were ionized by the electrospray technique of a LCQ classic mass spectrometer. Areas of the detected peaks of the peptides of the present invention were measured and used for quantification by external calibration. The calibration curve was linear over a range from 0.5 µg/ml to 250 µg/ml plasma. Half life—defined as the period for a concentration decrease to 50% of the initial concentration—was calculated from the slope of an extrapolated curve plotting the relative peptide concentration at a given time point (logarithm scale) against the incubation time. These experiments allowed the quantitative analysis of peptide concentration in plasma. The results obtained show a considerable half-life of peptides of the invention in humans, cynomolgus monkeys and dogs, while in vitro half-life in the rat appears to be short. The values obtained for $t_{1/2}$ in humans and the monkey demonstrate that peptides of the invention exhibit a sufficient half-life required for the inhibition of cellular infection by HIV particles and thus for therapeutical use against AIDS. The following table shows the calculated half-life of peptides of the invention in the corresponding plasma of humans, rat, dog and cynomolgus monkey.

TABLE 3

Half-lives of the peptides of the present invention in plasma of human, rat, dog and cynomolgus monkey.

| Peptide | $t_{1/2}$ human [h] | $t_{1/2}$ rat [h] | $t_{1/2}$ dog [h] | $t_{1/2}$ cynomolgus [h] |
|---|---|---|---|---|
| VIRIP | 53.7 | 1.7 | 35.9 | 5.1 |
| VIR-166 | 7.6 | 0.4 | 11 | 12.1 |
| VIR-175 | 5.3 | 0.2 | 17.3 | 3 |
| VIR-261 | 7 | 0.2 | 15.1 | 6.5 |
| VIR-273 | 4.2 | 0.1 | 12.4 | 3.6 |
| VIR-274 | 2 | 0.1 | 9.5 | 2.8 |
| VIR-344 | 7 | 0.1 | 6.6 | 10.5 |
| VIR-345 | 5.6 | 0.1 | 10.7 | 5.1 |
| VIR-348 | 3.3 | 0.2 | 9.3 | 3 |
| VIR-352 | 3.6 | 0.2 | 23.7 | 6.4 |
| VIR-353 | 4 | 0.2 | 15.2 | 5 |
| VIR-357 | 23.3 | 0.6 | 71.5 | 13.2 |
| VIR-358 | 5.9 | 0.4 | 16 | 4.7 |
| VIR-448 | 3.1 | 0.2 | 18 | 4.5 |
| VIR-449 | 4.8 | 0.2 | 42.2 | 4.2 |
| VIR-454 | 4.4 | 0.2 | 15.6 | 4.4 |
| VIR-455 | 5.8 | 0.3 | 8.6 | 6.8 |

TABLE 3-continued

Half-lives of the peptides of the present invention in plasma of human, rat, dog and cynomolgus monkey.

| Peptide | $t_{1/2}$ human [h] | $t_{1/2}$ rat [h] | $t_{1/2}$ dog [h] | $t_{1/2}$ cynomolgus [h] |
|---|---|---|---|---|
| VIR-483 | 2.6 | 0.2 | 6.2 | 2.2 |
| VIR-484 | 5 | 0.2 | 12.4 | 3.6 |
| VIR-512 | 315 | >6 | 48.1 | 33.6 |
| VIR-568 | 3.9 | 0.1 | 4 | 2.2 |
| VIR-576 | 5.8 | 2.6 | 12.6 | 3.8 |
| VIR-580 | 38.9 | 1.4 | 42 | 10.2 |

Example 6

Inhibition of fusion Peptide-Induced Hemolysis

The synthetic fusion peptide of HIV gp41 causes concentration-dependent hemolysis which can be measured by hemoglobin released by erythrocytes.

Peptides and any other substance binding to the fusion peptide impair its potency to lyse erythrocytes by changing its structural properties. The inhibition of fusion peptide induced hemolysis was tested as follows: Blood from healthy donors was collected in citrate monovettes and the erythrocytes were extracted by a standard centrifugation and washing protocol known to the skilled person. The final erythrocyte-containing pellett was diluted 1:100 with phosphate-saline buffer. To the peptides (10, 100, or 1000 equivalents) 20 µl of a 100 µM fusion peptide solution in 10% DMSO were added and the solution was diluted to 100 µl with phosphate-buffered saline. A 60 min incubation at 37° C. was carried out. After the preincubation the samples were transferred to 96-well plates and 100 µl of the erythrocyte suspension were added and incubated for 60 min at 37° C. Total hemolysis was achieved with 1% Tween-20. The 96-well plate is centrifuged 5 min at 2800 rpm and of the supernatant fluid 150 µl were transferred to a flat-bottom microtiter plate, and the absorbance was measured at 450 nm. The percentage hemolysis was calculated by: [(A450 of the peptide treated sample—A450 of buffer treated sample)/(A450 of Tween-20 treated sample—A450 of buffer treated sample)]×100%.

The results show that the fusion peptide-induced hemolysis is inhibited upon addition of increasing concentrations of peptides of the invention. In particular, the fusion peptide-induced hemolysis is more effectively inhibited by peptides of the invention compared to VIRIP. These results demonstrate that peptides of the invention block cellular infection by HIV particles by interacting with the viral gp41 protein.

Abbreviations:
AIDS: aquired immuno-defincy syndrome
Boc: tert-butyloxycarbonyl
CXCR4: CXC chemokine receptor 4
CCR5: CC chemokine receptor 5
ESI-MS: electrospray ionization-mass spectrometry
FP: fusion peptide
HIV: human immunodeficiency virus
HPLC: high performance liquid chromatography
HR-1, HR-2: heptad repeat 1, 2
MALDI-TOF: matrix-assisted laser desorption/ionization-time-of-flight
Mini-PEG: —NH—$(CH_2)_2$—O—$(CH_2)_2$—O—$CH_2$—CO—NH—$(CH_2)_2$—O—$(CH_2)_2$—O—$CH_2$—CO—$NH_2$
NMR: nuclear magnetic resonance
Oic: octahydroindolyl-2-carboxylic acid
PEG: pegyl, polyoxyethyleneglycol
QSAR: quantitative structure-activity relationship
tBu: tert-butyl
TFA: trifluoroacetc acid
Tic: 1,2,3,4-tetrahydroisoquinoline-3-carboxylic acid
Trt: trityl

The invention claimed is:

1. A composition comprising, in combination with a medicinally acceptable carrier or diluent, a synthetic compound, wherein the compound is a peptide having amino acid sequence (LEAIPCSIPPEFLFGKPFVF)$_2$ (SEQ ID NO:86), or an amidated, alkylated, acylated, sulfated, pegylated, phosphorylated, or glycosylated derivative of the peptide.

2. The medicament of claim 1 in a galenic formulation for oral administration.

3. The medicament of claim 1 in a galenic formulation for intravenous, intramuscular, intracutaneous, subcutaneous, or intrathecal administration.

4. The medicament of claim 1 as an aerosol for transpulmonary administration.

5. The medicament of claim 1 further comprising at least one additional therapeutic agent.

6. The medicament of claim 1 further comprising at least one additional therapeutic agent, wherein the agent is a viral protease inhibitor, a reverse transcriptase inhibitor, a fusion inhibitor, a cytokine, a cytokine inhibitor, a glycosylation inhibitor, or a viral mRNA inhibitor.

7. A nucleic acid, wherein said nucleic acid encodes the peptide of claim 1.

* * * * *

UNITED STATES PATENT AND TRADEMARK OFFICE
CERTIFICATE OF CORRECTION

PATENT NO. : 7,655,629 B2
APPLICATION NO. : 10/539627
DATED : February 2, 2010
INVENTOR(S) : Adermann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 450 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,629 B2 | Page 1 of 1 |
| APPLICATION NO. | : 10/539627 | |
| DATED | : February 2, 2010 | |
| INVENTOR(S) | : Knut Adermann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 523 days.

Signed and Sealed this
Twenty-second Day of March, 2011

David J. Kappos
*Director of the United States Patent and Trademark Office*

```
SEQUENCE LISTING

<160> NUMBER OF SEQ ID NOS: 88

<210> SEQ ID NO 1
<211> LENGTH: 20
<212> TYPE: PRT
<213> ORGANISM: Homo sapiens

<400> SEQUENCE: 1

Leu Glu Ala Ile Pro Met Ser Ile Pro Pro Glu Val Lys Phe Asn Lys
 1               5                  10                  15

Pro Phe Val Phe
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: VIR-121
<220> FEATURE:
<221> NAME/KEY: MUTAGEN
<222> LOCATION: (10)
<223> OTHER INFORMATION: Xaa is D-proline

<400> SEQUENCE: 2
```

```
Leu Glu Ala Ile Pro Met Ser Ile Pro Xaa Glu Val Ala Phe Asn Lys
  1               5                  10                  15

Pro Phe Val Phe
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: VIR-161
<220> FEATURE:
<221> NAME/KEY: VARIANT
<222> LOCATION: (10)
<223> OTHER INFORMATION: Xaa is D-proline

<400> SEQUENCE: 3

Leu Glu Ala Ile Pro Cys Ser Ile Pro Xaa Cys Val Ala Phe Asn Lys
  1               5                  10                  15

Pro Phe Val Phe
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: VIR-162

<400> SEQUENCE: 4

Leu Glu Ala Ile Pro Cys Ser Ile Pro Pro Cys Val Gly Phe Gly Lys
  1               5                  10                  15

Pro Phe Val Phe
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: VIR-163

<400> SEQUENCE: 5

Leu Glu Ala Ile Pro Cys Ser Ile Pro Pro Cys Val Leu Phe Asn Lys
  1               5                  10                  15

Pro Phe Val Phe
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: VIR-164

<400> SEQUENCE: 6

Leu Glu Ala Ile Pro Cys Ser Ile Pro Pro Cys Val Phe Phe Asn Lys
  1               5                  10                  15

Pro Phe Val Phe
            20

<210> SEQ ID NO 7
<211> LENGTH: 20
<212> TYPE: PRT
<213> ORGANISM: Artificial Sequence
```

```
<220> FEATURE:
<223> OTHER INFORMATION: Description of Artificial Sequence: VIR-165

<400> SEQUENCE: 7

Leu Glu Ala Ile Pro Cys Ser Ile Pro Pro Cys Phe Ala Phe Asn Lys
 1               5                  10                  15

Pro Phe Val Phe
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: VIR-166
<220> FEATURE:
<221> NAME/KEY: MUTAGEN
<222> LOCATION: (14)
<223> OTHER INFORMATION: Xaa is D-Tic
<220> FEATURE:
<221> NAME/KEY: MUTAGEN
<222> LOCATION: (18)
<223> OTHER INFORMATION: Xaa is D-Tic

<400> SEQUENCE: 8

Leu Glu Ala Ile Pro Cys Ser Ile Pro Pro Cys Val Ala Xaa Asn Lys
 1               5                  10                  15

Pro Xaa Phe Val Phe
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: VIR-170

<400> SEQUENCE: 9

Leu Glu Ala Ile Pro Met Ser Ile Pro Pro Glu Val Phe Phe Gly Lys
 1               5                  10                  15

Pro Phe Val Phe
            20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: VIR-175

<400> SEQUENCE: 10

Leu Glu Ala Ile Pro Met Ser Ile Pro Pro Glu Phe Leu Phe Gly Lys
 1               5                  10                  15

Pro Phe Val Phe
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: VIR-182

<400> SEQUENCE: 11

Leu Glu Ala Ile Pro Met Ser Ile Pro Pro Glu Leu Ala Phe Ala Lys
 1               5                  10                  15
```

Pro Phe Val Phe
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: VIR-184

<400> SEQUENCE: 12

Leu Glu Ala Ile Pro Met Ser Ile Pro Pro Glu Ile Ala Phe Asn Lys
 1               5                  10                  15

Pro Phe Val Phe
            20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: VIR-190
<220> FEATURE:
<221> NAME/KEY: MUTAGEN
<222> LOCATION: (10)
<223> OTHER INFORMATION: Xaa is D-proline

<400> SEQUENCE: 13

Leu Glu Ala Ile Pro Met Ser Ile Pro Xaa Glu Val Gly Phe Gly Lys
 1               5                  10                  15

Pro Phe Val Phe
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: VIR-191
<220> FEATURE:
<221> NAME/KEY: MUTAGEN
<222> LOCATION: (10)
<223> OTHER INFORMATION: Xaa is D-proline

<400> SEQUENCE: 14

Leu Glu Ala Ile Pro Met Ser Ile Pro Xaa Glu Val Leu Phe Gly Lys
 1               5                  10                  15

Pro Phe Val Phe
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: VIR-192
<220> FEATURE:
<221> NAME/KEY: MUTAGEN
<222> LOCATION: (10)
<223> OTHER INFORMATION: Xaa is D-proline

<400> SEQUENCE: 15

Leu Glu Ala Ile Pro Met Ser Ile Pro Xaa Glu Val Phe Phe Gly Lys
 1               5                  10                  15

Pro Phe Val Phe
            20

-continued

```
<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: VIR-193
<220> FEATURE:
<221> NAME/KEY: MUTAGEN
<222> LOCATION: (10)
<223> OTHER INFORMATION: Xaa is D-proline

<400> SEQUENCE: 16

Leu Glu Ala Ile Pro Met Ser Ile Pro Xaa Glu Phe Ala Phe Asn Lys
 1               5                  10                  15

Pro Phe Val Phe
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: VIR-197
<220> FEATURE:
<221> NAME/KEY: MUTAGEN
<222> LOCATION: (10)
<223> OTHER INFORMATION: Xaa is a D-proline

<400> SEQUENCE: 17

Leu Glu Ala Ile Pro Met Ser Ile Pro Xaa Glu Val Phe Phe Asn Lys
 1               5                  10                  15

Pro Phe Val Phe
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: VIR-199
<220> FEATURE:
<221> NAME/KEY: MUTAGEN
<222> LOCATION: (10)
<223> OTHER INFORMATION: Xaa is D-proline

<400> SEQUENCE: 18

Leu Glu Ala Ile Pro Met Ser Ile Pro Xaa Glu Phe Leu Phe Asn Lys
 1               5                  10                  15

Pro Phe Val Phe
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: VIR-229
<220> FEATURE:
<221> NAME/KEY: MUTAGEN
<222> LOCATION: (10)
<223> OTHER INFORMATION: Xaa is D-proline

<400> SEQUENCE: 19

Leu Glu Ala Ile Pro Ile Ser Ile Pro Xaa Glu Val Ala Phe Asn Lys
 1               5                  10                  15

Pro Phe Val Phe
```

```
<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: VIR-234
<220> FEATURE:
<221> NAME/KEY: MUTAGEN
<222> LOCATION: (10)
<223> OTHER INFORMATION: Xaa is D-proline

<400> SEQUENCE: 20

Leu Glu Ala Ile Pro Met Gly Ile Pro Xaa Glu Val Ala Phe Asn Lys
 1               5                  10                  15

Pro Phe Val Phe
         20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: VIR-243

<400> SEQUENCE: 21

Leu Glu Ala Ile Pro Met Ser Ile Pro Pro Glu Phe Ala Phe Asn Lys
 1               5                  10                  15

Asp Phe Val Phe
         20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: VIR-252
<220> FEATURE:
<221> NAME/KEY: MUTAGEN
<222> LOCATION: (10)
<223> OTHER INFORMATION: Xaa is D-proline

<400> SEQUENCE: 22

Leu Glu Asp Ile Pro Met Ser Ile Pro Xaa Glu Val Ala Phe Asn Lys
 1               5                  10                  15

Pro Phe Val Phe
         20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: VIR-255
<220> FEATURE:
<221> NAME/KEY: MUTAGEN
<222> LOCATION: (10)
<223> OTHER INFORMATION: Xaa is D-proline

<400> SEQUENCE: 23

Leu Glu Lys Ile Pro Met Ser Ile Pro Xaa Glu Val Ala Phe Asn Lys
 1               5                  10                  15

Pro Phe Val Phe
         20
```

```
<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: VIR-257
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is cyclohexylalanine

<400> SEQUENCE: 24

Leu Glu Ala Ile Pro Met Ser Ile Pro Xaa Glu Val Xaa Phe Asn Lys
 1               5                  10                  15

Pro Phe Val Phe
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: VIR-258
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (12)
<223> OTHER INFORMATION: Xaa is 1-naphthylalanine

<400> SEQUENCE: 25

Leu Glu Ala Ile Pro Met Ser Ile Pro Xaa Glu Xaa Ala Phe Asn Lys
 1               5                  10                  15

Pro Phe Val Phe
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: VIR-259
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (12)
<223> OTHER INFORMATION: Xaa is p-fluorophenylalanine

<400> SEQUENCE: 26

Leu Glu Ala Ile Pro Met Ser Ile Pro Xaa Glu Xaa Ala Phe Asn Lys
 1               5                  10                  15

Pro Phe Val Phe
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: VIR-260
<220> FEATURE:
```

```
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is 4-pyridylalanine

<400> SEQUENCE: 27

Leu Glu Ala Ile Pro Met Ser Ile Pro Xaa Glu Val Xaa Phe Asn Lys
 1               5                  10                  15

Pro Phe Val Phe
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: VIR-261
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (12)
<223> OTHER INFORMATION: Xaa is 3,3-diphenylalanine

<400> SEQUENCE: 28

Leu Glu Ala Ile Pro Met Ser Ile Pro Xaa Glu Xaa Ala Phe Asn Lys
 1               5                  10                  15

Pro Phe Val Phe
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: VIR-262
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is D-Tic

<400> SEQUENCE: 29

Leu Glu Ala Ile Pro Met Ser Ile Pro Xaa Glu Val Xaa Phe Asn Lys
 1               5                  10                  15

Pro Phe Val Phe
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: VIR-263
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is L-Tic
```

```
<400> SEQUENCE: 30

Leu Glu Ala Ile Pro Met Ser Ile Pro Xaa Glu Val Xaa Phe Asn Lys
 1               5                  10                  15

Pro Phe Val Phe
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: VIR-264
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is 3-benzothienylalanine

<400> SEQUENCE: 31

Leu Glu Ala Ile Pro Met Ser Ile Pro Xaa Glu Val Xaa Phe Asn Lys
 1               5                  10                  15

Pro Phe Val Phe
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: VIR-265
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is 3-thienylalanine

<400> SEQUENCE: 32

Leu Glu Ala Ile Pro Met Ser Ile Pro Xaa Glu Val Xaa Phe Asn Lys
 1               5                  10                  15

Pro Phe Val Phe
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: VIR-266
<220> FEATURE:
<221> NAME/KEY: MUTAGEN
<222> LOCATION: (10)
<223> OTHER INFORMATION: Xaa ia D-proline

<400> SEQUENCE: 33

Leu Glu Ala Ile Pro Met Ser Ile Pro Xaa Glu Val Trp Phe Asn Lys
 1               5                  10                  15

Pro Phe Val Phe
            20

<210> SEQ ID NO 34
```

```
<211> LENGTH: 20
<212> TYPE: PRT
<213> ORGANISM: Artificial Sequence
<220> FEATURE:
<223> OTHER INFORMATION: Description of Artificial Sequence: VIR-268
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (17)
<223> OTHER INFORMATION: Xaa is L-Tic

<400> SEQUENCE: 34

Leu Glu Ala Ile Pro Met Ser Ile Pro Xaa Glu Val Ala Phe Asn Lys
 1               5                  10                  15

Xaa Phe Val Phe
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: VIR-269
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (17)
<223> OTHER INFORMATION: Xaa is Oic

<400> SEQUENCE: 35

Leu Glu Ala Ile Pro Met Ser Ile Pro Xaa Glu Val Ala Phe Asn Lys
 1               5                  10                  15

Xaa Phe Val Phe
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: VIR-272

<400> SEQUENCE: 36

Leu Glu Ala Ile Pro Met Cys Ile Pro Pro Glu Cys Leu Phe Asn Lys
 1               5                  10                  15

Pro Phe Val Phe
            20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: VIR-273

<400> SEQUENCE: 37

Leu Glu Ala Ile Pro Met Cys Ile Pro Pro Glu Cys Phe Phe Asn Lys
 1               5                  10                  15

Pro Phe Val Phe
            20
```

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: VIR-274

<400> SEQUENCE: 38

Leu Glu Ala Ile Pro Met Cys Ile Pro Pro Glu Cys Leu Phe Gly Lys
 1               5                  10                  15

Pro Phe Val Phe
            20

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: VIR-280

<400> SEQUENCE: 39

Leu Glu Ala Ile Pro Cys Ser Ile Pro Pro Cys Phe Leu Phe Gly Lys
 1               5                  10                  15

Pro Phe Val Phe
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: VIR-284

<400> SEQUENCE: 40

Leu Glu Ala Ile Pro Ile Ser Ile Pro Pro Glu Val Phe Phe Gly Lys
 1               5                  10                  15

Pro Phe Val Phe
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: VIR-286

<400> SEQUENCE: 41

Leu Glu Ala Ile Pro Ile Ser Ile Pro Pro Glu Leu Ala Phe Ala Lys
 1               5                  10                  15

Pro Phe Val Phe
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: VIR-290
<220> FEATURE:
<221> NAME/KEY: MUTAGEN
<222> LOCATION: (10)
<223> OTHER INFORMATION: Xaa is D-proline

<400> SEQUENCE: 42

Leu Glu Ala Ile Pro Ile Ser Ile Pro Xaa Glu Val Phe Phe Gly Lys
 1               5                  10                  15

```
Pro Phe Val Phe
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: VIR-298
<220> FEATURE:
<221> NAME/KEY: MUTAGEN
<222> LOCATION: (10)
<223> OTHER INFORMATION: Xaa is D-proline

<400> SEQUENCE: 43

Leu Glu Ala Ile Pro Ile Ser Ile Pro Xaa Glu Val Trp Phe Asn Lys
 1               5                  10                  15

Pro Phe Val Phe
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: VIR-320
<220> FEATURE:
<221> NAME/KEY: MUTAGEN
<222> LOCATION: (10)
<223> OTHER INFORMATION: Xaa is D-proline

<400> SEQUENCE: 44

Leu Glu Ala Ile Pro Met Gly Ile Pro Xaa Glu Val Phe Phe Gly Lys
 1               5                  10                  15

Pro Phe Val Phe
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: VIR-322
<220> FEATURE:
<221> NAME/KEY: MUTAGEN
<222> LOCATION: (10)
<223> OTHER INFORMATION: Xaa is D-proline

<400> SEQUENCE: 45

Leu Glu Ala Ile Pro Met Gly Ile Pro Xaa Glu Val Phe Phe Asn Lys
 1               5                  10                  15

Pro Phe Val Phe
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: VIR-323
<220> FEATURE:
<221> NAME/KEY: MUTAGEN
<222> LOCATION: (10)
<223> OTHER INFORMATION: Xaa is D-proline

<400> SEQUENCE: 46

Leu Glu Ala Ile Pro Met Gly Ile Pro Xaa Glu Phe Leu Phe Asn Lys
```

```
                1               5                  10                 15

Pro Phe Val Phe
            20

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: VIR-326
<220> FEATURE:
<221> NAME/KEY: MUTAGEN
<222> LOCATION: (10)
<223> OTHER INFORMATION: Xaa is D-proline

<400> SEQUENCE: 47

Leu Glu Asp Ile Pro Met Gly Ile Pro Xaa Glu Val Ala Phe Asn Lys
  1               5                  10                 15

Pro Phe Val Phe
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: VIR-328
<220> FEATURE:
<221> NAME/KEY: MUTAGEN
<222> LOCATION: (10)
<223> OTHER INFORMATION: Xaa is D-proline

<400> SEQUENCE: 48

Leu Glu Ala Ile Pro Met Gly Ile Pro Xaa Glu Val Trp Phe Asn Lys
  1               5                  10                 15

Pro Phe Val Phe
            20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: VIR-344

<400> SEQUENCE: 49

Leu Glu Ala Ile Pro Cys Ser Ile Pro Pro Cys Val Phe Phe Gly Lys
  1               5                  10                 15

Pro Phe Val Phe
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: VIR-345

<400> SEQUENCE: 50

Leu Glu Ala Ile Pro Cys Ser Ile Pro Pro Cys Phe Leu Phe Gly Lys
  1               5                  10                 15

Pro Phe Val Phe
            20

<210> SEQ ID NO 51
```

```
<211> LENGTH: 20
<212> TYPE: PRT
<213> ORGANISM: Artificial Sequence
<220> FEATURE:
<223> OTHER INFORMATION: Description of Artificial Sequence: VIR-346

<400> SEQUENCE: 51

Leu Glu Ala Ile Pro Cys Ser Ile Pro Pro Cys Leu Ala Phe Ala Lys
 1               5                  10                  15

Pro Phe Val Phe
            20

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: VIR-348
<220> FEATURE:
<221> NAME/KEY: MUTAGEN
<222> LOCATION: (10)
<223> OTHER INFORMATION: Xaa is D-proline

<400> SEQUENCE: 52

Leu Glu Ala Ile Pro Cys Ser Ile Pro Xaa Cys Val Gly Phe Gly Lys
 1               5                  10                  15

Pro Phe Val Phe
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: VIR-350
<220> FEATURE:
<221> NAME/KEY: MUTAGEN
<222> LOCATION: (10)
<223> OTHER INFORMATION: Xaa is D-proline

<400> SEQUENCE: 53

Leu Glu Ala Ile Pro Cys Ser Ile Pro Xaa Cys Val Phe Phe Gly Lys
 1               5                  10                  15

Pro Phe Val Phe
            20

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: VIR-351
<220> FEATURE:
<221> NAME/KEY: MUTAGEN
<222> LOCATION: (10)
<223> OTHER INFORMATION: Xaa is D-proline

<400> SEQUENCE: 54

Leu Glu Ala Ile Pro Cys Ser Ile Pro Xaa Cys Phe Ala Phe Asn Lys
 1               5                  10                  15

Pro Phe Val Phe
            20

<210> SEQ ID NO 55
<211> LENGTH: 20
<212> TYPE: PRT
<213> ORGANISM: Artificial Sequence
```

-continued

```
<220> FEATURE:
<223> OTHER INFORMATION: Description of Artificial Sequence: VIR-352
<220> FEATURE:
<221> NAME/KEY: MUTAGEN
<222> LOCATION: (10)
<223> OTHER INFORMATION: Xaa is D-proline

<400> SEQUENCE: 55

Leu Glu Ala Ile Pro Cys Ser Ile Pro Xaa Cys Val Phe Phe Asn Lys
  1               5                  10                  15

Pro Phe Val Phe
            20

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: VIR-353
<220> FEATURE:
<221> NAME/KEY: MUTAGEN
<222> LOCATION: (10)
<223> OTHER INFORMATION: Xaa is D-proline

<400> SEQUENCE: 56

Leu Glu Ala Ile Pro Cys Ser Ile Pro Xaa Cys Phe Leu Phe Asn Lys
  1               5                  10                  15

Pro Phe Val Phe
            20

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: VIR-354
<220> FEATURE:
<221> NAME/KEY: MUTAGEN
<222> LOCATION: (10)
<223> OTHER INFORMATION: Xaa is D-proline

<400> SEQUENCE: 57

Leu Glu Ala Ile Pro Cys Ser Ile Pro Xaa Cys Val Ala Phe Asn Lys
  1               5                  10                  15

Pro Phe Val Phe
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: VIR-355
<220> FEATURE:
<221> NAME/KEY: MUTAGEN
<222> LOCATION: (10)
<223> OTHER INFORMATION: Xaa is D-proline

<400> SEQUENCE: 58

Leu Glu Ala Ile Pro Cys Gly Ile Pro Xaa Cys Val Ala Phe Asn Lys
  1               5                  10                  15

Pro Phe Val Phe
            20

<210> SEQ ID NO 59
<211> LENGTH: 20
<212> TYPE: PRT
```

<213> ORGANISM: Artificial Sequence
<220> FEATURE:
<223> OTHER INFORMATION: Description of Artificial Sequence: VIR-356

<400> SEQUENCE: 59

Leu Glu Ala Ile Pro Cys Ser Ile Pro Pro Cys Phe Ala Phe Asn Lys
 1               5                  10                  15

Asp Phe Val Phe
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: VIR-357
<220> FEATURE:
<221> NAME/KEY: MUTAGEN
<222> LOCATION: (10)
<223> OTHER INFORMATION: Xaa is D-proline

<400> SEQUENCE: 60

Leu Glu Asp Ile Pro Cys Ser Ile Pro Xaa Cys Val Ala Phe Asn Lys
 1               5                  10                  15

Pro Phe Val Phe
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: VIR-358
<220> FEATURE:
<221> NAME/KEY: MUTAGEN
<222> LOCATION: (10)
<223> OTHER INFORMATION: Xaa is D-proline

<400> SEQUENCE: 61

Leu Glu Lys Ile Pro Cys Ser Ile Pro Xaa Cys Val Ala Phe Asn Lys
 1               5                  10                  15

Pro Phe Val Phe
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: VIR-376
<220> FEATURE:
<221> NAME/KEY: MUTAGEN
<222> LOCATION: (10)
<223> OTHER INFORMATION: Xaa is D-proline

<400> SEQUENCE: 62

Leu Glu Ala Ile Pro Met Ser Ile Pro Xaa Glu Phe Leu Phe Gly Lys
 1               5                  10                  15

Pro Ala Phe Val Phe
            20

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: VIR-377

```
<220> FEATURE:
<221> NAME/KEY: MUTAGEN
<222> LOCATION: (10)
<223> OTHER INFORMATION: Xaa is D-proline

<400> SEQUENCE: 63

Leu Glu Ala Ile Pro Met Ser Ile Pro Xaa Glu Phe Leu Phe Gly Lys
 1               5                  10                  15

Pro Gly Phe Val Phe
            20

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: VIR-380
<220> FEATURE:
<221> NAME/KEY: MUTAGEN
<222> LOCATION: (10)
<223> OTHER INFORMATION: Xaa is D-proline

<400> SEQUENCE: 64

Leu Glu Ala Ile Pro Met Ser Ile Pro Xaa Glu Phe Leu Phe Gly Lys
 1               5                  10                  15

Pro Phe Phe Val Phe
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: VIR-384
<220> FEATURE:
<221> NAME/KEY: MUTAGEN
<222> LOCATION: (10)
<223> OTHER INFORMATION: Xaa is D-proline

<400> SEQUENCE: 65

Leu Glu Ala Ile Pro Met Ser Ile Pro Xaa Glu Phe Leu Phe Gly Lys
 1               5                  10                  15

Pro Glu Phe Val Phe
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: VIR-396
<220> FEATURE:
<221> NAME/KEY: MUTAGEN
<222> LOCATION: (10)
<223> OTHER INFORMATION: Xaa is D-proline

<400> SEQUENCE: 66

Leu Glu Ala Ile Pro Met Ser Ala Pro Xaa Glu Phe Leu Phe Gly Lys
 1               5                  10                  15

Pro Phe Val Phe
            20

<210> SEQ ID NO 67
<211> LENGTH: 20
<212> TYPE: PRT
<213> ORGANISM: Artificial Sequence
<220> FEATURE:
```

```
<223> OTHER INFORMATION: Description of Artificial Sequence: VIR-400
<220> FEATURE:
<221> NAME/KEY: MUTAGEN
<222> LOCATION: (10)
<223> OTHER INFORMATION: Xaa is D-proline

<400> SEQUENCE: 67

Leu Glu Ala Ile Pro Met Ser Phe Pro Xaa Glu Phe Leu Phe Gly Lys
 1               5                  10                  15

Pro Phe Val Phe
         20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: VIR-416
<220> FEATURE:
<221> NAME/KEY: MUTAGEN
<222> LOCATION: (10)
<223> OTHER INFORMATION: Xaa is D-proline

<400> SEQUENCE: 68

Leu Glu Ala Ile Pro Met Gly Ile Pro Xaa Glu Phe Leu Phe Gly Lys
 1               5                  10                  15

Pro Phe Val Phe
         20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: VIR-418
<220> FEATURE:
<221> NAME/KEY: MUTAGEN
<222> LOCATION: (10)
<223> OTHER INFORMATION: Xaa is D-proline

<400> SEQUENCE: 69

Leu Glu Lys Ile Pro Met Gly Ile Pro Xaa Glu Phe Leu Phe Gly Lys
 1               5                  10                  15

Pro Phe Val Phe
         20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: VIR-445
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is D-Tic

<400> SEQUENCE: 70

Leu Glu Ala Ile Pro Ile Ser Ile Pro Xaa Pro Glu Val Xaa Phe Asn
 1               5                  10                  15

Lys Pro Phe Val Phe
         20
```

-continued

```
<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: VIR-447
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (17)
<223> OTHER INFORMATION: Xaa is L-Tic

<400> SEQUENCE: 71

Leu Glu Ala Ile Pro Ile Ser Ile Pro Xaa Glu Val Ala Phe Asn Lys
 1               5                  10                  15

Xaa Phe Val Phe
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: VIR-448
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is D-Tic

<400> SEQUENCE: 72

Leu Glu Ala Ile Pro Met Gly Ile Pro Xaa Glu Val Xaa Phe Asn Lys
 1               5                  10                  15

Pro Phe Val Phe
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: VIR-449
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is L-Tic

<400> SEQUENCE: 73

Leu Glu Ala Ile Pro Met Gly Ile Pro Xaa Glu Val Xaa Phe Asn Lys
 1               5                  10                  15

Pro Phe Val Phe
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: VIR-452
<220> FEATURE:
```

```
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is L-Tic

<400> SEQUENCE: 74

Leu Glu Asp Ile Pro Met Ser Ile Pro Xaa Glu Val Xaa Phe Asn Lys
  1               5                  10                  15

Pro Phe Val Phe
            20

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: VIR-454
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is D-Tic

<400> SEQUENCE: 75

Leu Glu Lys Ile Pro Met Ser Ile Pro Xaa Glu Val Xaa Phe Asn Lys
  1               5                  10                  15

Pro Phe Val Phe
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: VIR-455
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is L-Tic

<400> SEQUENCE: 76

Leu Glu Lys Ile Pro Met Ser Ile Pro Xaa Glu Val Xaa Phe Asn Lys
  1               5                  10                  15

Pro Phe Val Phe
            20

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: VIR-479
<220> FEATURE:
<221> NAME/KEY: MUTAGEN
<222> LOCATION: (10)
<223> OTHER INFORMATION: Xaa is D-proline

<400> SEQUENCE: 77

Leu Glu Asp Ile Pro Ile Gly Ile Pro Xaa Glu Phe Leu Phe Asn Lys
```

```
                1               5                  10                 15
Pro Phe Val Phe
            20

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: VIR-483
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is D-Tic

<400> SEQUENCE: 78

Leu Glu Lys Ile Pro Ile Gly Ile Pro Xaa Glu Val Xaa Phe Asn Lys
 1               5                  10                 15
Pro Phe Val Phe
            20

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: VIR-484
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is L-Tic

<400> SEQUENCE: 79

Leu Glu Lys Ile Pro Ile Gly Ile Pro Xaa Glu Val Xaa Phe Asn Lys
 1               5                  10                 15
Pro Phe Val Phe
            20

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: VIR-485
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (17)
<223> OTHER INFORMATION: Xaa is L-Tic

<400> SEQUENCE: 80

Leu Glu Lys Ile Pro Ile Gly Ile Pro Xaa Glu Val Ala Phe Asn Lys
 1               5                  10                 15
Xaa Phe Val Phe
            20

<210> SEQ ID NO 81
```

```
<211> LENGTH: 20
<212> TYPE: PRT
<213> ORGANISM: Artificial Sequence
<220> FEATURE:
<223> OTHER INFORMATION: Description of Artificial Sequence: VIR-487
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (13)
<223> OTHER INFORMATION: Xaa is L-Tic

<400> SEQUENCE: 81

Leu Glu Asp Ile Pro Ile Gly Ile Pro Xaa Glu Val Xaa Phe Asn Lys
  1               5                  10                  15

Pro Phe Val Phe
           20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: VIR-488
<220> FEATURE:
<221> NAME/KEY: MUTAGEN
<222> LOCATION: (10)
<223> OTHER INFORMATION: Xaa is D-proline
<220> FEATURE:
<221> NAME/KEY: MUTAGEN
<222> LOCATION: (17)
<223> OTHER INFORMATION: Xaa is L-Tic

<400> SEQUENCE: 82

Leu Glu Asp Ile Pro Ile Gly Ile Pro Xaa Glu Val Ala Phe Asn Lys
  1               5                  10                  15

Xaa Phe Val Phe
           20

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: VIR-512
<220> FEATURE:
<221> NAME/KEY: MUTAGEN
<222> LOCATION: (1)
<223> OTHER INFORMATION: Xaa is N-methyl-leucine

<400> SEQUENCE: 83

Xaa Glu Ala Ile Pro Met Ser Ile Pro Pro Glu Phe Leu Phe Gly Lys
  1               5                  10                  15

Pro Phe Val Phe
           20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: VIR-568

<400> SEQUENCE: 84

Leu Glu Ala Ile Pro Met Ser Cys Pro Pro Glu Phe Cys Phe Gly Lys
  1               5                  10                  15
```

```
Pro Phe Val Phe
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: VIR-570

<400> SEQUENCE: 85

Leu Glu Ala Ile Pro Cys Ser Ile Pro Pro Glu Cys Leu Phe Gly Lys
  1               5                  10                  15

Pro Phe Val Phe
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: VIR-576
<220> FEATURE:
<221> NAME/KEY: DISULFID
<222> LOCATION: (6)
<223> OTHER INFORMATION: An intermolecular disulfide bridge forms
      between the  cysteine residues of two VIR-576, giving rise
      to a homo-dimer.

<400> SEQUENCE: 86

Leu Glu Ala Ile Pro Cys Ser Ile Pro Pro Glu Phe Leu Phe Gly Lys
  1               5                  10                  15

Pro Phe Val Phe
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: VIR-580
<220> FEATURE:
<221> NAME/KEY: BINDING
<222> LOCATION: (20)
<223> OTHER INFORMATION: Mini-PEG rest is bound to phenylalanine;
      Mini-PEG = -NH-(CH2)2-O-(CH2)2-O-CH2-CO-NH-(CH2)2-O-(CH2)2-O-
      CH2-CO-NH2

<400> SEQUENCE: 87

Leu Glu Ala Ile Pro Met Ser Ile Pro Pro Glu Phe Leu Phe Gly Lys
  1               5                  10                  15

Pro Phe Val Phe
            20

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: VIR-590

<400> SEQUENCE: 88

Leu Glu Ala Ile Pro Met Lys Ile Pro Pro Glu Phe Leu Phe Gly Lys
  1               5                  10                  15

Pro Phe Val Phe
            20
```